US006582415B1

(12) United States Patent
Fowles et al.

(10) Patent No.: US 6,582,415 B1
(45) Date of Patent: *Jun. 24, 2003

(54) SLIDING RECONSTITUTION DEVICE FOR A DILUENT CONTAINER

(76) Inventors: Thomas A. Fowles, 3420 Chellington Dr., McHenry, IL (US) 60050; Robert J. Weinberg, 1008 Front St., McHenry, IL (US) 60050

( * ) Notice: Subject to any disclaimer, the term of this patent is extended or adjusted under 35 U.S.C. 154(b) by 0 days.

This patent is subject to a terminal disclaimer.

(21) Appl. No.: 09/561,666

(22) Filed: May 2, 2000

Related U.S. Application Data

(63) Continuation of application No. 09/153,816, filed on Sep. 15, 1998, now Pat. No. 6,113,583.

(51) Int. Cl.[7] ............................ A61B 19/00; E03B 1/00
(52) U.S. Cl. ................... 604/413; 604/414; 137/614.04
(58) Field of Search ......................... 604/403, 411–416, 604/200, 201, 88, 533–535; 137/614.04

(56) References Cited

U.S. PATENT DOCUMENTS

| | | | |
|---|---|---|---|
| 3,330,281 | A | 7/1967 | Visser |
| 3,330,282 | A | 7/1967 | Visser et al. |
| 3,336,924 | A | 8/1967 | Sarnoff et al. |
| 3,785,481 | A | 1/1974 | Allet-Coche |
| 3,796,303 | A | 3/1974 | Allet-Coche |
| 3,809,225 | A | 5/1974 | Allet-Coche |
| 3,917,063 | A | 11/1975 | Chibret et al. |
| 4,014,330 | A | 3/1977 | Genese |
| 4,031,895 | A | 6/1977 | Porter |
| 4,059,112 | A | 11/1977 | Tischlinger |
| 4,116,196 | A | 9/1978 | Kaplan et al. |
| 4,170,994 | A | 10/1979 | Komatsu |
| 4,210,142 | A | 7/1980 | Wörder |
| 4,210,173 | A | 7/1980 | Choksi et al. |
| 4,226,330 | A | 10/1980 | Butler |
| 4,243,080 | A | 1/1981 | Choksi et al. |
| 4,247,651 | A | 1/1981 | Ohno et al. |
| 4,270,533 | A | 6/1981 | Andreas |
| 4,303,071 | A | 12/1981 | Smith |
| 4,328,802 | A | 5/1982 | Curley et al. |
| 4,392,850 | A | 7/1983 | Elias et al. |
| 4,396,383 | A | 8/1983 | Hart |
| 4,410,321 | A | 10/1983 | Pearson et al. |

(List continued on next page.)

FOREIGN PATENT DOCUMENTS

| | | |
|---|---|---|
| DE | 1913926 | 9/1970 |
| DE | 1766151 | 3/1971 |
| EP | 0 022 977 A1 | 1/1981 |

(List continued on next page.)

*Primary Examiner*—Angela D. Sykes
*Assistant Examiner*—Leslie R Deak
(74) *Attorney, Agent, or Firm*—Paul J. Nykaza; Wallenstein & Wagner

(57) ABSTRACT

A connector device is disclosed for establishing fluid communication between a diluent container having sidewalls and a drug vial. The connector has a piercing member having a first end and a second end and a central fluid pathway. The piercing member is mounted to the liquid container and has fluid accessing portions hermetically sealed from an outside environment. A vial receiving chamber is associated with the piercing member and is dimensioned to connect to the vial. The vial may be selectively attached to the device without piercing the closure of the vial and without breaching the hermetic seal of the fluid accessing portions of the piercing member. Means are provided for connecting the vial receiving chamber to the liquid container. The device is movable from an inactivated position, where the piercing member is outside the sidewalls and no fluid flows between the liquid container and the drug vial, to an activated position, where fluid flows through the fluid pathway between the liquid container and the drug vial. The device is movable from the inactivated position to the activated position by a force applied to the device outside the liquid container.

44 Claims, 11 Drawing Sheets

U.S. PATENT DOCUMENTS

| | | | |
|---|---|---|---|
| 4,411,358 | A | 10/1983 | Bennwik et al. |
| 4,411,662 | A | 10/1983 | Pearson |
| 4,424,056 | A | 1/1984 | Urquhart et al. |
| 4,424,057 | A | 1/1984 | House |
| 4,432,754 | A | 2/1984 | Urquhart et al. |
| 4,432,755 | A | 2/1984 | Pearson |
| 4,432,756 | A | 2/1984 | Urquhart et al. |
| 4,439,182 | A | 3/1984 | Huang |
| 4,439,183 | A | 3/1984 | Theeuwes |
| 4,458,733 | A | 7/1984 | Lyons |
| 4,458,811 | A | 7/1984 | Wilkinson |
| 4,465,471 | A | 8/1984 | Harris et al. |
| 4,465,488 | A | 8/1984 | Richmond et al. |
| 4,467,588 | A | 8/1984 | Carveth |
| 4,469,872 | A | 9/1984 | Anderson et al. |
| 4,474,574 | A | 10/1984 | Wolfe et al. |
| 4,479,793 | A | 10/1984 | Urquhart et al. |
| 4,479,794 | A | 10/1984 | Urquhart et al. |
| 4,484,909 | A | 11/1984 | Urquhart et al. |
| 4,484,920 | A | 11/1984 | Kaufman et al. |
| 4,493,703 | A | 1/1985 | Butterfield |
| 4,496,646 | A | 1/1985 | Ito |
| 4,505,709 | A | 3/1985 | Froning et al. |
| 4,507,113 | A | 3/1985 | Dunlap |
| 4,507,114 | A | 3/1985 | Bohman et al. |
| 4,511,351 | A | 4/1985 | Theeuwes |
| 4,511,352 | A | 4/1985 | Theeuwes et al. |
| 4,511,353 | A | 4/1985 | Theeuwes |
| 4,515,351 | A | 5/1985 | Nakayama et al. |
| 4,515,585 | A | 5/1985 | Urquhart et al. |
| 4,516,967 | A | 5/1985 | Kopfer |
| 4,516,977 | A | 5/1985 | Herbert |
| 4,518,386 | A | 5/1985 | Tartaglia |
| 4,519,499 | A | 5/1985 | Stone et al. |
| 4,521,211 | A | 6/1985 | Theeuwes |
| 4,525,162 | A | 6/1985 | Urquhart et al. |
| 4,533,348 | A | 8/1985 | Wolfe et al. |
| 4,534,757 | A | 8/1985 | Geller |
| 4,534,758 | A | 8/1985 | Akers et al. |
| 4,538,918 | A | 9/1985 | Mittleman |
| 4,539,793 | A | 9/1985 | Malek |
| 4,540,089 | A | 9/1985 | Maloney |
| 4,540,403 | A | 9/1985 | Theeuwes |
| 4,543,094 | A | 9/1985 | Barnwell |
| 4,543,101 | A | 9/1985 | Crouch |
| 4,548,598 | A | 10/1985 | Theeuwes |
| 4,548,599 | A | 10/1985 | Urquhart et al. |
| 4,548,606 | A | 10/1985 | Larkin |
| 4,550,825 | A | 11/1985 | Sutryn et al. |
| 4,552,277 | A | 11/1985 | Richardson et al. |
| 4,552,555 | A | 11/1985 | Theeuwes |
| 4,552,556 | A | 11/1985 | Urquhart et al. |
| 4,561,110 | A | 12/1985 | Herbert |
| 4,564,054 | A | 1/1986 | Gustavsson |
| 4,568,331 | A | 2/1986 | Fischer et al. |
| 4,568,336 | A | 2/1986 | Cooper |
| 4,568,346 | A | 2/1986 | van Dijk |
| 4,573,967 | A | 3/1986 | Hargrove et al. |
| 4,573,993 | A | 3/1986 | Hoag et al. |
| 4,576,211 | A | 3/1986 | Valentini et al. |
| 4,579,553 | A | 4/1986 | Urquhart et al. |
| 4,581,016 | A | 4/1986 | Gettig |
| 4,583,971 | A | 4/1986 | Bocquet et al. |
| 4,583,981 | A | 4/1986 | Urquhart et al. |
| 4,586,922 | A | 5/1986 | Theeuwes |
| 4,589,867 | A | 5/1986 | Israel |
| 4,589,879 | A | 5/1986 | Pearson |
| 4,590,234 | A | 5/1986 | Tasaka et al. |
| 4,596,555 | A | 6/1986 | Theeuwes |
| 4,601,704 | A | 7/1986 | Larkin |
| 4,602,910 | A | 7/1986 | Larkin |
| 4,606,734 | A | 8/1986 | Larkin et al. |
| 4,607,671 | A | 8/1986 | Aalto et al. |
| 4,608,043 | A | 8/1986 | Larkin |
| 4,610,684 | A | 9/1986 | Knox et al. |
| 4,613,326 | A | 9/1986 | Szwarc |
| 4,614,267 | A | 9/1986 | Larkin |
| 4,614,515 | A | 9/1986 | Tripp et al. |
| 4,623,334 | A | 11/1986 | Riddell |
| 4,629,080 | A | 12/1986 | Carveth |
| 4,630,727 | A | 12/1986 | Feriani et al. |
| 4,632,244 | A | 12/1986 | Landau |
| 4,637,934 | A | 1/1987 | White |
| 4,650,475 | A | 3/1987 | Smith et al. |
| 4,662,878 | A | 5/1987 | Lindmayer |
| 4,664,650 | A | 5/1987 | Urquhart et al. |
| 4,668,219 | A | 5/1987 | Israel |
| 4,673,404 | A | 6/1987 | Gustavsson |
| 4,675,020 | A | 6/1987 | McPhee |
| 4,692,144 | A | 9/1987 | Carpenter |
| 4,693,706 | A | 9/1987 | Ennis, III |
| 4,695,272 | A | 9/1987 | Berglund et al. |
| 4,703,864 | A | 11/1987 | Larkin et al. |
| 4,715,854 | A | 12/1987 | Vaillancourt |
| 4,717,388 | A | 1/1988 | Steer et al. |
| 4,722,733 | A | 2/1988 | Howson |
| 4,723,956 | A | 2/1988 | Schnell et al. |
| 4,727,985 | A | 3/1988 | McNeirney et al. |
| 4,731,053 | A | 3/1988 | Hoffman |
| 4,735,608 | A | 4/1988 | Sardam |
| 4,740,103 | A | 4/1988 | Theeuwes |
| 4,740,197 | A | 4/1988 | Theeuwes |
| 4,740,198 | A | 4/1988 | Theeuwes |
| 4,740,199 | A | 4/1988 | Theeuwes |
| 4,740,200 | A | 4/1988 | Theeuwes |
| 4,740,201 | A | 4/1988 | Theeuwes |
| 4,741,734 | A | 5/1988 | Theeuwes |
| 4,741,735 | A | 5/1988 | Theeuwes |
| 4,743,229 | A | 5/1988 | Chu |
| 4,747,834 | A | 5/1988 | Prindle |
| 4,752,292 | A | 6/1988 | Lopez et al. |
| 4,757,911 | A | 7/1988 | Larkin et al. |
| 4,759,756 | A | 7/1988 | Forman et al. |
| 4,778,453 | A | 10/1988 | Lopez |
| 4,781,679 | A | 11/1988 | Larkin |
| 4,782,841 | A | 11/1988 | Lopez |
| 4,784,259 | A | 11/1988 | Grabenkort |
| 4,784,658 | A | 11/1988 | Grabenkort |
| 4,785,858 | A | 11/1988 | Valentini et al. |
| 4,786,279 | A | 11/1988 | Wilkinson et al. |
| 4,787,429 | A | 11/1988 | Valentini et al. |
| 4,790,820 | A | 12/1988 | Theeuwes |
| 4,804,360 | A | 2/1989 | Kamen |
| 4,804,366 | A | 2/1989 | Zdeb et al. |
| 4,808,381 | A | 2/1989 | McGregor et al. |
| 4,816,024 | A | 3/1989 | Sitar et al. |
| 4,819,659 | A | 4/1989 | Sitar |
| 4,820,269 | A | 4/1989 | Riddell |
| 4,822,351 | A | 4/1989 | Purcell |
| 4,832,690 | A | 5/1989 | Kuu |
| 4,834,149 | A | 5/1989 | Fournier et al. |
| 4,834,152 | A | 5/1989 | Howson et al. |
| 4,842,028 | A | 6/1989 | Kaufman et al. |
| 4,850,978 | A | 7/1989 | Dudar et al. |
| 4,857,052 | A | 8/1989 | Theeuwes |
| 4,861,335 | A | 8/1989 | Reynolds |
| 4,861,585 | A | 8/1989 | Galef, Jr. et al. |
| 4,865,354 | A | 9/1989 | Allen |
| 4,871,354 | A | 10/1989 | Conn et al. |
| 4,871,360 | A | 10/1989 | Theeuwes |
| 4,871,463 | A | 10/1989 | Taylor et al. |

| | | | |
|---|---|---|---|
| 4,872,494 | A | 10/1989 | Coccia |
| 4,874,366 | A | 10/1989 | Zdeb et al. |
| 4,874,368 | A | 10/1989 | Miller et al. |
| 4,883,483 | A | 11/1989 | Lindmayer |
| 4,886,495 | A | 12/1989 | Reynolds |
| 4,898,209 | A | 2/1990 | Zbed |
| 4,906,103 | A | 3/1990 | Kao |
| 4,908,019 | A | 3/1990 | Urquhart et al. |
| 4,909,290 | A | 3/1990 | Coccia |
| 4,911,708 | A | 3/1990 | Maezaki et al. |
| 4,915,689 | A | 4/1990 | Theeuwes |
| 4,927,013 | A | 5/1990 | Van Brunt et al. |
| 4,927,423 | A | 5/1990 | Malmborg |
| 4,927,605 | A | 5/1990 | Dorn et al. |
| 4,931,048 | A | 6/1990 | Lopez |
| 4,936,445 | A | 6/1990 | Grabenkort |
| 4,936,829 | A | 6/1990 | Zdeb et al. |
| 4,936,841 | A | 6/1990 | Aoki et al. |
| 4,944,736 | A | 7/1990 | Holtz |
| 4,948,000 | A | 8/1990 | Grabenkort |
| 4,950,237 | A | 8/1990 | Henault et al. |
| 4,961,495 | A | 10/1990 | Yoshida et al. |
| 4,968,299 | A | 11/1990 | Ahlstrand et al. |
| 4,969,883 | A | 11/1990 | Gilbert et al. |
| 4,973,307 | A | 11/1990 | Theeuwes |
| 4,978,337 | A | 12/1990 | Theeuwes |
| 4,979,942 | A | 12/1990 | Wolf et al. |
| 4,982,875 | A | 1/1991 | Pozzi et al. |
| 4,983,164 | A | 1/1991 | Hook et al. |
| 4,985,016 | A | 1/1991 | Theeuwes et al. |
| 4,986,322 | A | 1/1991 | Chibret et al. |
| 4,994,031 | A | 2/1991 | Theeuwes |
| 4,994,056 | A | 2/1991 | Ikeda |
| 4,996,579 | A | 2/1991 | Chu |
| 4,997,083 | A | 3/1991 | Loretti et al. |
| 4,997,430 | A | 3/1991 | Van der Heiden et al. |
| 5,002,530 | A | 3/1991 | Recker et al. |
| 5,023,119 | A | 6/1991 | Yamakoshi |
| 5,024,657 | A | 6/1991 | Needham et al. |
| 5,030,203 | A | 7/1991 | Wolf, Jr. et al. |
| 5,032,117 | A | 7/1991 | Motta |
| 5,045,081 | A | 9/1991 | Dysarz |
| 5,049,129 | A | 9/1991 | Zdeb et al. |
| 5,049,135 | A | 9/1991 | Davis |
| 5,061,264 | A | 10/1991 | Scarrow |
| 5,064,059 | A | 11/1991 | Ziegler et al. |
| 5,069,671 | A | 12/1991 | Theeuwes |
| 5,074,844 | A | 12/1991 | Zdeb et al. |
| 5,074,849 | A | 12/1991 | Sachse |
| D323,389 | S | 1/1992 | Aoki et al. |
| 5,080,652 | A | 1/1992 | Sancoff et al. |
| 5,084,040 | A | 1/1992 | Sutter |
| 5,088,996 | A | 2/1992 | Kopfer et al. |
| 5,100,394 | A | 3/1992 | Dudar et al. |
| 5,102,408 | A | 4/1992 | Hamacher |
| 5,104,375 | A | 4/1992 | Wolf et al. |
| 5,114,004 | A | 5/1992 | Isono et al. |
| 5,114,411 | A | 5/1992 | Haber et al. |
| 5,116,315 | A | 5/1992 | Capozzi et al. |
| 5,116,316 | A | 5/1992 | Sertic et al. |
| 5,117,875 | A | 6/1992 | Marrucchi |
| 5,122,123 | A | 6/1992 | Vaillancourt |
| 5,125,892 | A | 6/1992 | Drudik |
| 5,125,908 | A | 6/1992 | Cohen |
| 5,126,175 | A | 6/1992 | Yamakoshi |
| 5,129,894 | A | 7/1992 | Sommermeyer et al. |
| 5,137,511 | A | 8/1992 | Reynolds |
| 5,147,324 | A | 9/1992 | Skakoon et al. |
| 5,152,965 | A | 10/1992 | Fisk et al. |
| 5,156,598 | A | 10/1992 | Skakoon et al. |
| 5,158,546 | A | 10/1992 | Haber et al. |
| 5,160,320 | A | 11/1992 | Yum et al. |
| 5,167,642 | A | 12/1992 | Fowles |
| 5,169,388 | A | 12/1992 | McPhee |
| 5,171,214 | A | 12/1992 | Kolber et al. |
| 5,171,219 | A | 12/1992 | Fujioka et al. |
| 5,171,220 | A | 12/1992 | Morimoto |
| 5,176,634 | A | 1/1993 | Smith et al. |
| 5,176,673 | A | 1/1993 | Marrucchi |
| 5,181,909 | A | 1/1993 | McFarlane |
| 5,186,323 | A | 2/1993 | Pfleger |
| 5,188,615 | A | 2/1993 | Haber et al. |
| 5,188,629 | A | 2/1993 | Shimoda |
| 5,195,658 | A | 3/1993 | Hoshino |
| 5,195,986 | A | 3/1993 | Kamen |
| 5,196,001 | A | 3/1993 | Kao |
| 5,199,947 | A | 4/1993 | Lopez et al. |
| 5,199,948 | A | 4/1993 | McPhee |
| 5,200,200 | A | 4/1993 | Veech |
| 5,201,705 | A | 4/1993 | Berglund et al. |
| 5,207,509 | A | 5/1993 | Herbert |
| 5,209,201 | A | 5/1993 | Horie et al. |
| 5,209,347 | A | 5/1993 | Fabisiewicz et al. |
| 5,211,201 | A | 5/1993 | Kamen et al. |
| 5,211,285 | A | 5/1993 | Haber et al. |
| 5,222,946 | A | 6/1993 | Kamen |
| 5,226,878 | A | 7/1993 | Young |
| 5,226,900 | A | 7/1993 | Bancsi et al. |
| RE34,365 | E | 8/1993 | Theeuwes |
| 5,232,029 | A | 8/1993 | Knox et al. |
| 5,232,109 | A | 8/1993 | Tirrell et al. |
| 5,246,142 | A | 9/1993 | DiPalma et al. |
| 5,247,972 | A | 9/1993 | Tetreault |
| 5,250,028 | A | 10/1993 | Theeuwes et al. |
| 5,257,985 | A | 11/1993 | Puhl |
| 5,257,986 | A | 11/1993 | Herbert et al. |
| 5,257,987 | A | 11/1993 | Athayde et al. |
| 5,259,843 | A | 11/1993 | Watanabe et al. |
| 5,259,954 | A | 11/1993 | Taylor |
| 5,261,902 | A | 11/1993 | Okada et al. |
| 5,267,646 | A | 12/1993 | Inoue et al. |
| 5,267,957 | A | 12/1993 | Kriesel et al. |
| 5,279,576 | A | 1/1994 | Loo et al. |
| 5,279,579 | A | 1/1994 | D'Amico |
| 5,279,583 | A | 1/1994 | Shober, Jr. et al. |
| 5,281,198 | A | 1/1994 | Haber et al. |
| 5,281,206 | A | 1/1994 | Lopez |
| 5,286,257 | A | 2/1994 | Fischer |
| 5,287,961 | A | 2/1994 | Herran |
| 5,289,585 | A | 2/1994 | Kock et al. |
| 5,302,603 | A | 4/1994 | Crawley et al. |
| 5,303,751 | A | 4/1994 | Slater et al. |
| 5,304,130 | A | 4/1994 | Button et al. |
| 5,304,163 | A | 4/1994 | Bonnici et al. |
| 5,304,165 | A | 4/1994 | Haber et al. |
| 5,306,242 | A | 4/1994 | Joyce et al. |
| 5,308,287 | A | 5/1994 | Gunsing |
| 5,308,347 | A | 5/1994 | Sunago et al. |
| 5,320,603 | A | 6/1994 | Vetter et al. |
| 5,328,464 | A | 7/1994 | Kriesel et al. |
| 5,330,048 | A | 7/1994 | Haber et al. |
| 5,330,426 | A | 7/1994 | Kriesel et al. |
| 5,330,450 | A | 7/1994 | Lopez |
| 5,330,462 | A | 7/1994 | Nakamura |
| 5,330,464 | A | 7/1994 | Mathias et al. |
| 5,332,399 | A | 7/1994 | Grabenkort et al. |
| 5,334,178 | A | 8/1994 | Haber et al. |
| 5,334,180 | A | 8/1994 | Adolf et al. |
| 5,334,188 | A | 8/1994 | Inoue et al. |
| 5,335,773 | A | 8/1994 | Haber et al. |
| 5,336,180 | A | 8/1994 | Kriesel et al. |
| 5,342,346 | A | 8/1994 | Honda et al. |

| | | | | |
|---|---|---|---|---|
| 5,342,347 A | | 8/1994 | Kikuchi et al. | |
| 5,344,414 A | | 9/1994 | Lopez et al. | |
| 5,348,060 A | | 9/1994 | Futagawa et al. | |
| 5,348,600 A | | 9/1994 | Ishii | |
| 5,350,372 A | | 9/1994 | Ikeda et al. | |
| 5,350,546 A | | 9/1994 | Takeuchi et al. | |
| 5,352,191 A | | 10/1994 | Sunago et al. | |
| 5,352,196 A | | 10/1994 | Haber et al. | |
| 5,352,210 A | | 10/1994 | Marrucchi | |
| 5,353,961 A | | 10/1994 | Debush | |
| 5,356,380 A | | 10/1994 | Hoekwater et al. | |
| 5,358,501 A | | 10/1994 | Meyer | |
| 5,360,410 A | | 11/1994 | Wacks | |
| 5,364,350 A | | 11/1994 | Dittmann | |
| 5,364,369 A | | 11/1994 | Reynolds | |
| 5,364,371 A | | 11/1994 | Kamen | |
| 5,364,384 A | | 11/1994 | Grabenkort et al. | |
| 5,368,586 A | | 11/1994 | Van Der Heiden et al. | |
| 5,370,164 A | | 12/1994 | Galloway | |
| 5,373,966 A | | 12/1994 | O'Reilly et al. | |
| 5,374,264 A | | 12/1994 | Wadsworth, Jr. | |
| 5,376,079 A | | 12/1994 | Holm | |
| 5,380,281 A | | 1/1995 | Tomellini et al. | |
| 5,380,315 A | | 1/1995 | Isono et al. | |
| 5,385,545 A | | 1/1995 | Kriesel et al. | |
| 5,385,546 A | | 1/1995 | Kriesel et al. | |
| 5,385,547 A | | 1/1995 | Wong et al. | |
| 5,386,372 A | | 1/1995 | Kobayashi et al. | |
| 5,393,497 A | | 2/1995 | Haber et al. | |
| 5,397,303 A | | 3/1995 | Sancoff et al. | |
| 5,398,851 A | | 3/1995 | Sancoff et al. | |
| 5,401,253 A | | 3/1995 | Reynolds | |
| 5,409,141 A | | 4/1995 | Kikuchi et al. | |
| 5,423,421 A | | 6/1995 | Inoue et al. | |
| 5,423,753 A | | 6/1995 | Fowles et al. | |
| 5,423,793 A | | 6/1995 | Isono et al. | |
| 5,423,796 A | | 6/1995 | Shikhman et al. | |
| 5,425,447 A | | 6/1995 | Farina | |
| 5,425,528 A | | 6/1995 | Rains et al. | |
| 5,429,256 A | | 7/1995 | Kestenbaum | |
| 5,429,603 A | | 7/1995 | Morris | |
| 5,429,614 A | | 7/1995 | Fowles et al. | |
| 5,435,076 A | | 7/1995 | Hjertman et al. | |
| 5,445,631 A | | 8/1995 | Uchida | |
| 5,458,593 A | | 10/1995 | Macabasco et al. | |
| 5,462,526 A | | 10/1995 | Barney et al. | |
| 5,464,123 A | | 11/1995 | Scarrow | |
| 5,470,327 A | | 11/1995 | Helgren et al. | |
| 5,472,022 A | | 12/1995 | Michel et al. | |
| 5,472,422 A | | 12/1995 | Ljungquist | |
| 5,474,540 A | | 12/1995 | Miller et al. | |
| 5,478,337 A | | 12/1995 | Okamoto et al. | |
| 5,484,406 A | | 1/1996 | Wong et al. | |
| 5,484,410 A | | 1/1996 | Kriesel et al. | |
| 5,489,266 A | | 2/1996 | Grimard | |
| 5,490,848 A | | 2/1996 | Finley et al. | |
| 5,492,147 A | | 2/1996 | Challender et al. | |
| 5,492,219 A | | 2/1996 | Stupar | |
| 5,493,774 A | | 2/1996 | Grabenkort | |
| 5,494,190 A | | 2/1996 | Boettcher | |
| 5,501,887 A | | 3/1996 | Tanaka et al. | |
| 5,509,898 A | | 4/1996 | Isono et al. | |
| 5,510,115 A | | 4/1996 | Breillatt, Jr. et al. | |
| 5,514,090 A | | 5/1996 | Kriesel et al. | |
| 5,520,972 A | | 5/1996 | Ezaki et al. | |
| 5,522,804 A | | 6/1996 | Lynn | |
| 5,526,853 A | | 6/1996 | McPhee et al. | |
| 5,531,683 A | | 7/1996 | Kriesel et al. | |
| 5,533,389 A | | 7/1996 | Kamen et al. | |
| 5,533,973 A | | 7/1996 | Piontek et al. | |
| 5,533,994 A | | 7/1996 | Meyer | |
| 5,535,746 A | | 7/1996 | Hoover et al. | |
| 5,536,469 A | | 7/1996 | Jonsson et al. | |
| 5,538,506 A | | 7/1996 | Farris et al. | |
| 5,540,674 A | | 7/1996 | Karas et al. | |
| 5,547,471 A | | 8/1996 | Thompson et al. | |
| 5,554,125 A | | 9/1996 | Reynolds | |
| 5,554,128 A | | 9/1996 | Hedges | |
| 5,560,403 A | | 10/1996 | Balteau et al. | |
| 5,566,729 A | | 10/1996 | Grabenkort et al. | |
| 5,569,191 A | | 10/1996 | Meyer | |
| 5,569,192 A | | 10/1996 | van der Wal | |
| 5,573,527 A | | 11/1996 | Macabasco et al. | |
| 5,575,310 A | | 11/1996 | Kamen et al. | |
| 5,577,369 A | | 11/1996 | Becker et al. | |
| 5,584,808 A | | 12/1996 | Healy | |
| 5,593,028 A | | 1/1997 | Haber et al. | |
| 5,595,314 A | | 1/1997 | Weiler | |
| 5,596,193 A | | 1/1997 | Chutjian et al. | |
| 5,603,695 A | | 2/1997 | Erickson | |
| 5,603,696 A | | 2/1997 | Williams et al. | |
| 5,605,542 A | | 2/1997 | Tanaka et al. | |
| 5,611,792 A | | 3/1997 | Gustafsson | |
| 5,620,434 A | | 4/1997 | Brony | |
| 5,624,405 A | | 4/1997 | Futagawa et al. | |
| 5,641,010 A | | 6/1997 | Maier | |
| 5,669,891 A | * | 9/1997 | Vaillancourt | 604/411 |
| 5,688,254 A | | 11/1997 | Lopez et al. | |
| 5,709,666 A | | 1/1998 | Reynolds | |
| 5,827,262 A | | 10/1998 | Neftel et al. | |
| 5,897,526 A | | 4/1999 | Vaillancourt | |
| 5,989,237 A | | 11/1999 | Fowles et al. | |
| 6,019,750 A | | 2/2000 | Fowles et al. | |
| 6,022,339 A | * | 2/2000 | Fowles et al. | 604/411 |
| 6,063,068 A | * | 5/2000 | Fowles et al. | 604/411 |
| 6,071,270 A | * | 6/2000 | Fowles et al. | 137/614.04 |
| 6,090,092 A | * | 7/2000 | Fowles et al. | 604/413 |

FOREIGN PATENT DOCUMENTS

| | | | |
|---|---|---|---|
| EP | 0 091 310 | A2 | 12/1983 |
| EP | 0 285 424 | A1 | 5/1988 |
| EP | 0 335 378 | A2 | 4/1989 |
| EP | 0 363 770 | A1 | 4/1990 |
| EP | 0 395 758 | A1 | 7/1990 |
| EP | 0 499 764 | A1 | 8/1991 |
| EP | 0 692 235 | A1 | 7/1994 |
| GB | 2 211 104 | A | 6/1989 |
| WO | WO 83/03540 | | 10/1983 |
| WO | WO 85/03432 | | 8/1985 |
| WO | WO 90/03536 | | 4/1990 |
| WO | WO 92/11897 | | 7/1992 |
| WO | WO 93/02723 | | 2/1993 |
| WO | WO 93/09825 | | 5/1993 |
| WO | WO 97/25015 | | 7/1997 |

* cited by examiner

SLIDING RECONSTITUTION DEVICE FOR A DILUENT CONTAINER

This is a continuation of application Ser. No. 09/153,816, filed Sep. 15, 1998, U.S. Pat. No. 6,113,583 which is incorporated herein by reference and made a part hereof, and upon which a claim of priority is based.

TECHNICAL FIELD

The present invention relates generally to the delivery of a beneficial agent to a patient. More specifically, the present invention relates to an improved device for reconstituting a beneficial agent to be delivered to a patient.

BACKGROUND OF THE INVENTION

Many drugs are unstable even for a short period of time in a dissolved state and therefore are packaged, stored, and shipped in a powdered or lyophilized state to increase their shelf life. In order for powdered drugs to be given intravenously to a patient, the drugs must first be placed in liquid form. To this end, these drugs are mixed or reconstituted with a diluent before being delivered intravenously to a patient. The diluents may be, for example, a dextrose solution, a saline solution, or even water. Typically the drugs are stored in powdered form in glass vials or ampules.

Other drugs, although in a liquid state, must still be diluted before administering to a patient. For example, some chemotherapy drugs are stored in glass vials or ampules, in a liquid state, but must be diluted prior to use. As used herein, reconstitution means to place the powdered drug in a liquid state, as well as, the dilution of a liquid drug.

The reconstitution procedure should be performed under sterile conditions. In some procedures for reconstituting, maintaining sterile conditions is difficult. Moreover, some drugs, such as chemotherapy drugs, are toxic and exposure to the medical personnel during the reconstitution procedure can be dangerous. One way of reconstituting a powdered drug is to inject the liquid diluent directly into the drug vial. This can be performed by use of a combination-syringe and syringe needle having diluent therein. In this regard, drug vials typically include a pierceable rubber stopper. The rubber stopper of the drug vial is pierced by the needle, and liquid in the syringe is then injected into the vial. The vial is shaken to mix the powdered drug with the liquid. After the liquid and drug are mixed, a measured amount of the reconstituted drug is then drawn into the syringe. The syringe is then withdrawn from the vial and the drug can then be injected into the patient. Another method of drug administration is to inject the reconstituted drug, contained in the syringe, into a parenteral solution container. Examples of such containers include a MINI-BAG™ flexible parenteral solution container or VIAFLEX® flexible parenteral solution container sold by Baxter Healthcare Corporation of Deerfield, Ill. These parenteral solution containers may already have therein dextrose or saline solutions. The reconstituted drug is injected into the container, mixed with the solution in the parenteral solution container and delivered through an intravenous solution administration set to a vein access site of the patient.

Another method for reconstituting a powdered drug utilizes a reconstitution device sold by Baxter Healthcare Corporation, product code No. 2B8064. That device includes a double pointed needle and guide tubes mounted around both ends of the needle. This reconstitution device is utilized to place the drug vial in fluid communication with a flexible-walled parenteral solution container. Once the connection is made by piercing a port of the flexible container with one end of the needle and the vial stopper with the other end of the needle, liquid in the solution container may be forced through the needle into the drug vial by squeezing the sidewalls of the solution container. The vial is then shaken to mix the liquid and drug. The liquid in the vial is withdrawn by squeezing air from the solution container into the vial. When compression of the flexible walled solution container is stopped, the pressurized air in the vial acts as a pump to force the liquid in the vial back into the solution container.

An improvement to this product is the subject of commonly assigned U.S. Pat. No. 4,607,671 to Aalto et al. The device of the '671 patent includes a series of bumps on the inside of a sheath to grip a drug vial. These bumps hinder the inadvertent disconnection of the device with the vial.

U.S. Pat. No. 4,759,756 discloses a reconstitution device which, in an embodiment, includes an improved vial adaptor and bag adaptor that permit the permanent coupling of a vial and liquid container. The bag adaptor is rotatable relative to the vial adaptor to either block fluid communication in a first position or effect fluid communication in a second position.

Another form of reconstitution device is seen in commonly assigned U.S. Pat. No. 3,976,073 to Quick et al. Yet another type of reconstitution device is disclosed in U.S. Pat. No. 4,328,802 to Curley et al., entitled "Wet-Dry Syringe Package" which includes a vial adaptor having inwardly directed retaining projections to firmly grip the retaining cap lip of a drug vial to secure the vial to the vial adaptor. The package disclosed by Curley et al. is directed to reconstituting a drug by use of a liquid-filled syringe.

Other methods for reconstituting a drug are shown, for example, in commonly assigned U.S. Pat. No. 4,410,321 to Pearson et al., entitled "Close Drug Delivery System"; U.S. Pat. Nos. 4,411,662 and 4,432,755 to Pearson, both entitled "Sterile Coupling"; U.S. Pat. No. 4,458,733 to Lyons entitled "Mixing Apparatus"; and U.S. Pat. No. 4,898,209 to Zdeb entitled "Sliding Reconstitution Device With Seal."

Other related patents include U.S. Pat. No. 4,872,867 to Kilinger entitled "Wet-Dry Additive Assembly"; U.S. Pat. No. 3,841,329 to Kilinger entitled "Compact Syringe"; U.S. Pat. No. 3,826,261 to Kilinger entitled "Vial and Syringe Assembly"; U.S. Pat. No. 3,826,260 to Kilinger entitled "Vial and Syringe Combination"; U.S. Pat. No. 3,378,369 to Kilinger entitled "Apparatus for Transferring Liquid Between a Container and a Flexible Bag"; and German specification DE OS 36 27 231.

Commonly assigned U.S. Pat. No. 4,898,209 to Zdeb (the '209 Patent), discloses a sliding reconstitution device which solved some of the problems discussed above. For example, the connector allowed for preattaching the device to a vial without piercing a closure of the vial. However, no seal was provided on the opposite end of the connector so the vial and device assembly had to be used immediately after connection or stored in a sterile environment, such as under a hood.

The '209 Patent discloses a first sleeve member that is mounted concentrically about a second sleeve member. The sleeve members can be moved axially with respect to each other to cause a needle or cannula to pierce a drug container and a diluent container to place the containers in fluid communication with each other.

The process for using the '209 connector required three distinct steps. The sleeves had to be rotated with respect to one another to move the device into an unlocked position. The sleeves were then moved axially with respect to one another to an activated position to pierce closures of the containers. The sleeves had to be rotated again to lock the sleeves in the activated position.

However, it is possible for the device of the '209 Patent to be easily and inadvertently disassembled when being moved to the activated position. The second sleeve is capable of sliding entirely though the first sleeve member and becoming disassociated into separate parts. This would require the medical personnel to either reassemble the device or dispose of it due to contamination.

Also, the device of the '209 Patent did not provide for a visual indication that the device was in the activated position. It was also possible for the device to be inadvertently moved to the inactivated position, by rotating the first and second sleeve members in a direction opposite of the third step described above.

Additionally, it was possible for the second container, which is frequently a vial, to rotate within the device. This could cause coring of the vial stopper which could lead to leakage of the vial stopper. Additionally it was possible for a vial to be misaligned while being attached to the device causing the attachment process to be difficult for medical personnel. Further, the connector only releasably attached to the vial. Removal of the vial could remove all tamper evident indications that the reconstitution step has occurred and could lead to a second unintended dosage of medicine to be administered. Finally, the seal had a sleeve that covered only a portion of the cannula. The sleeve of the seal was relatively resilient and had the tendency of pushing the connector away from the drug container when docked thereto.

Yet another connector for attaching a drug vial to a parenteral solution container is disclosed in U.S. Pat. No. 4,675,020 ("the '020 patent"). The '020 patent discloses a connector having an end that docks to a drug vial and an opposite end that connects to the solution container. A shoulder and an end surface of the vial are held between first and second jaws of the vial end of the connector. The second jaws 71 terminate in a relatively sharp point that digs into and deforms the outermost end surface 94 of the vial sufficiently to accommodate dimensional variations between the shoulder and the outermost end surface of the vial. The marks that are left in the deformable end surface of the vial are intended to provide a tamper evident feature. However, tamper evident marks will not be left in vials that have a cap that is too short to impinge upon the sharp points.

The connector has a spike 25 that penetrates stoppers on the vial and on the solution container to place these containers in fluid communication. However, because the spike 25 extends outward beyond skirt sections 57, the connector of the '020 patent cannot be preattached to the fluid container or the drug container without piercing the stoppers of each. (The '020 patent states that the connector may be preassembled onto a drug vial, but there is no explanation of the structure of such a device. (Col. 6, lines 40–49)). This is undesirable as it initiates the time period in which the drug must be used, and typically this is a short period relative to the normal shelf-life of the product.

Also, the connector of the '020 patent does not provide a structure for preventing a docked vial from rotating. A closure of the vial can become damaged or cored upon rotation, which in turn, can lead to particles from the closure from entering the fluid that eventually passes to a patient. It can also lead to leakage of the closure of the vial.

Another connector for attaching a drug vial to a flexible container is disclosed in commonly assigned U.S. patent application Ser. No. 08/986,580. This connector has a piercing member mounted between two sleeves slidably mounted to one another. The bag connecting end is sealed by a peelable seal material. The seal material must be removed before connecting to the flexible container. Removal of the seal material exposes the piercing member to the outside environment thereby breaching the hermetic seal of the piercing member.

Another connector for attaching a drug vial to a flexible solution container is disclosed in U.S. Pat. No. 5,352,191 ("the '191 Patent"). The connector has a communicating portion having a communicating passage disposed at a top portion of the flexible container wherein one end of the communicating portion extends into the flexible container. The drug vial is fitted partially or wholly into an opposite end of the communicating portion. A membrane is disposed in the communicating passage for closing the passage. The connector also includes a puncturing needle unit mounted in the communicating passage for enabling the drug vial and flexible container to communicate with each other. When the puncturing needle unit is pressed externally through the flexible container, the needle breaks the membrane and opening of the drug vial to enable the drug vial and container to communicate with each other.

U.S. Pat. No. 5,380,315 and EP 0843992 disclose another connector for attaching a drug vial to a flexible solution container. Similar to the '191 patent, this patent and patent application have a communication device in the form of spike that is mounted within the flexible container. The communication device is externally pressed towards a drug vial to puncture the drug vial and communicate the drug vial with the flexible container.

U.S. Pat. No. 5,478,337 discloses a device for connecting a vial to a flexible container. This patent require the vial to be shipped pre-assembled to the connector, and, therefore, does not allow for medical personnel to selectively attach a vial to the connector.

Finally, U.S. Pat. No. 5,364,386 discloses a device for connecting a vial to a medical fluid container. The device includes a screw cap 32 that must be removed before inserting the vial. Removing the screw cap, however, potentially exposes the piercing member 48 to contaminants as the piercing member is not hermetically sealed.

SUMMARY OF THE INVENTION

The present invention provides a fluid reconstitution device for placing a first container, such as a diluent container (e.g. flexible container or syringe), in fluid communication with a second container, such as a drug vial. To this end, there is provided a connector device for establishing fluid communication between the diluent container having sidewalls and a drug vial. The connector has a piercing member having a first end and a second end and a central fluid pathway. The piercing member is mounted to the liquid container and has fluid accessing portions hermetically sealed from an outside environment. A vial receiving chamber is associated with the piercing member and is dimensioned to connect to the vial. The vial may be selectively attached to the device without piercing the closure of the vial and without breaching the hermetic seal of the fluid accessing portions of the piercing member. Means are provided for connecting the vial receiving chamber to the liquid container. The device is movable from an inactivated position, where the piercing member is outside the sidewalls and no fluid flows between the liquid container and the drug vial, to an activated position, where fluid flows through the fluid pathway between the liquid container and the drug vial. The device is movable from the inactivated position to the activated position by a force applied to the device outside the liquid container.

According to another aspect of the invention, there is provided a connector device having a first sleeve having a first end and a second end. The second end of the sleeve supports an interface seal member. The first sleeve has, at the first end, a port connector adapted to attach to the first container. The connector also has a second sleeve having a first end and a second end. The second end has an attaching member adapted to attach the second sleeve to the second container. The first sleeve is slidably mounted within the second sleeve from an inactivated position to activated position wherein the interface seal member slides along an inner surface of the second sleeve providing a seal between the first sleeve and the second sleeve. The connector further has a piercing assembly slidable within the second sleeve. The piercing assembly has a piercing member having a first end and a second end. The piercing member is positioned within the first sleeve and the second sleeve for providing fluid communication between the first container and the second container.

According to a further aspect of the invention, the first sleeve of the connector has a guide that receives the first end of the piercing member.

According to another aspect of the invention the connector has a disk positioned adjacent the port connector. The disk is positioned between the port connector and the guide. The first end of the piercing member pierces through the disk when the connector is in the activated position.

According to a further aspect of the invention, the connector is positioned to a post reconstitution position, or deactivated position, wherein the first end of the piercing member is pulled out of the disk and guide.

According to yet another aspect of the invention, a gasket is positioned within the first sleeve adjacent the port connector. The gasket is an x-ring gasket. The first end of the piercing member is positioned through the gasket. The gasket has a first end and a second end defining a length therebetween. The length of the gasket is dimensioned such that the piercing member at the second end of the gasket when the connector is in the inactivated position does not move past the first end of the gasket when the connector is placed in the activated position.

According to a further aspect of the invention, the attaching member has a pull-tab adapted to be removed before attaching the second container.

According to another embodiment of the invention, a connector device is provided having a sleeve having a first end and a second end. A piercing member is connected to the first end of the sleeve and is adapted to be connected to the first container. The piercing member is positioned within the sleeve and provides a fluid flow passage from the first container to the second container. A cup assembly is connected to the second end of the sleeve and is adapted to be attached to the second container. The sleeve is slidable with respect to the piercing member from an inactivated position to an activated position wherein the sleeve slides along the piercing member and folds upon itself. The piercing member pierces a closure of the second container establishing fluid communication between the first container and the second container.

According to another aspect of the invention, the sleeve has a first section and a second section, the first section having a greater diameter than the second section, wherein when the sleeve moves from the inactivated position to the activated position, the second section slides along the piercing member and the first section folds upon the second section.

According to a further aspect of the invention, the cup assembly comprises a base connected to a wall portion. The wall portion has a plurality of fingers inwardly spaced from the wall portion and are adapted to cooperatively receive the second container. The base is connected to the sleeve.

According to another aspect of the invention, a sealing member is positioned between a bottom portion of each finger and the base. In a preferred embodiment, the sealing member is a pierceable septum. The septum has a disk that is pierced by the piercing member when the sleeve is moved from the inactivated position to the activated position. The disk further has a generally centrally disposed annular ring extending axially from the disk. The annular ring is dimensioned to fit over a closure of the second container.

According to another aspect of the invention, the piercing member has a radial slot spaced from the fluid flow passage allowing contents of the first container to pass through the radial slot and into contact with an inner surface of the sleeve. In a preferred embodiment, the sleeve has a first section and a second section wherein the first section has a greater diameter than the second section. The contents of the first container can pass through the radial slot and into contact with an inner surface of the sleeve at the first section.

According to another aspect of the invention, the first end of the sleeve has an annular slot and the piercing member includes a collar having an annular ridge. The collar is connected to the sleeve wherein the annular slot receives the annular ridge. The collar is adapted to be attached to the first container.

According to yet another aspect of the invention, the sleeve has a second end sealed by a membrane. The membrane is positioned between the piercing member and the cup assembly and is pierced by the piercing member when the sleeve is moved from the inactivated position to the activated position.

According to another aspect of the invention, a seal material is releasably secured to the cup assembly. The seal material is selected from the group consisting of a foil, a polymeric material and a paper.

Other features and advantages of the invention will become apparent from the following description taken in conjunction with the following drawings.

DETAILED DESCRIPTION OF THE PREFERRED EMBODIMENTS

Figure 1:
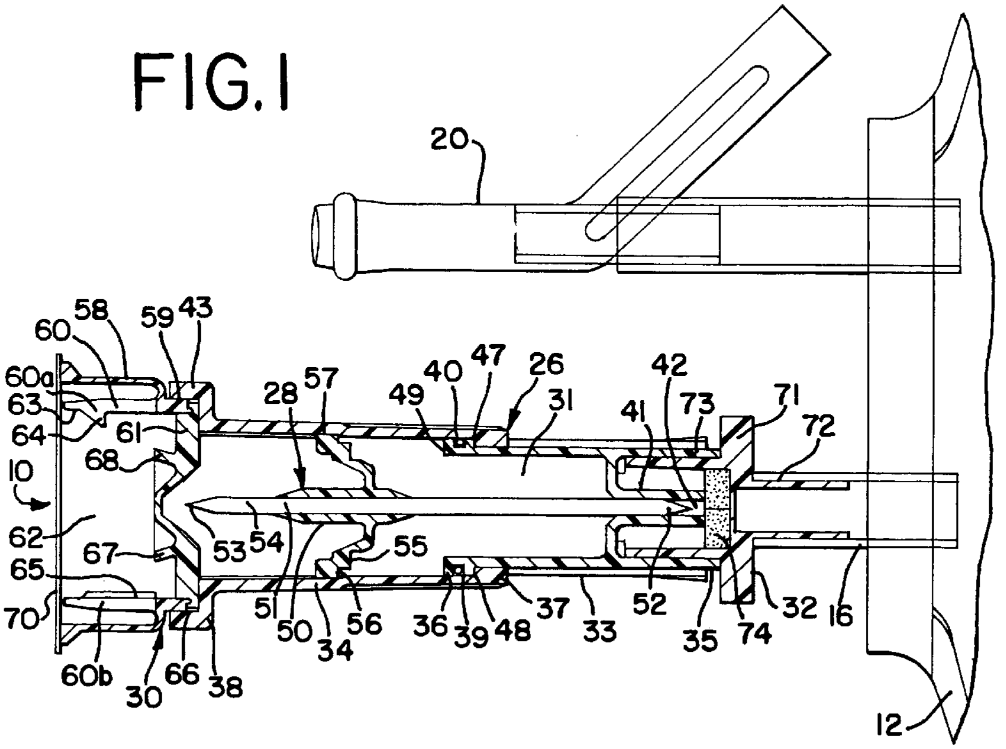
FIG. 1 is a cross sectional view of the connector device of the present invention attached to a flexible container.

While the invention is susceptible of embodiment in many different forms, there is shown in the drawings and will herein be described in detail preferred embodiments of the invention. It is to be understood that the present disclosure is to be considered as an exemplification of the principles of the invention. This disclosure is not intended to limit the broad aspect of the invention to the illustrated embodiments.

The present invention provides a connector device that is used to mix two substances within separate containers. More particularly, the invention provides a device to reconstitute a drug with a diluent. To accomplish the reconstitution of the drug, the invention provides an improved connecting device for attaching to a first container, commonly a flexible bag or a syringe, containing a diluent, to a second container, commonly a vial containing a drug to be reconstituted. The connector provides fluid communication between the two containers through a hermetically sealed piercing member so that the drug may be reconstituted, and delivered to a patient. What is meant by hermetically sealed is that the portions of the piercing member that contact the fluid and that pierce the closures of the two containers are sealed from the outside environment.

While the diluent will be a liquid, the beneficial agent may be either a powder or a lyophilized drug to be dissolved or a liquid drug to be reduced in concentration. The devices of the present invention provide the benefit of allowing medical personnel to selectively attach a vial of their choice to the connector. Thus, hospitals and pharmacies do not have to stock pre-packaged drug vial and connector assemblies. Further, the connectors of the present invention allow for docking a vial to the connector without breaching the hermetic seal of a piercing member associated with the connector and without piercing the closure of the vial. Thus, a vial may be pre-docked to the device of the present invention for essentially the full period the drug is active. Further, the devices of the present invention can be activated by applying a force directly to the connector without necessarily contacting sidewalls of the first and second containers.

Figure 3:
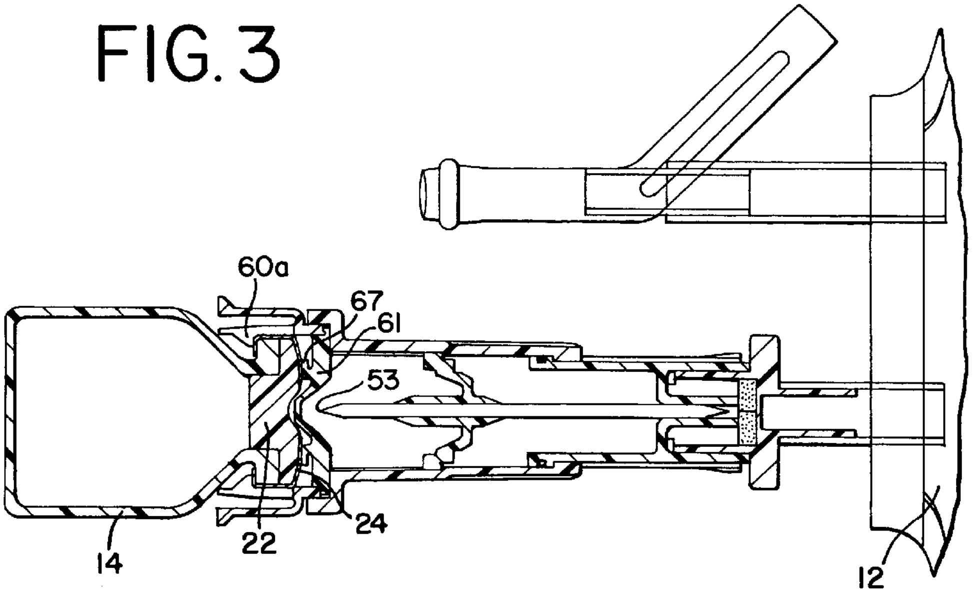
FIG. 3 is cross-sectional view of the connector device having a drug vial fixedly secured to the connector device, the connector device being in an inactivated position.

Referring to FIGS. 1 and 3, a connector device is disclosed and generally referred to with the reference numeral 10. The device 10 is adapted to place a first container 12, containing a liquid to be used as a diluent, in fluid communication with a second container 14, containing a drug to be diluted or reconstituted.

The first container 12 is typically a flexible bag and is used to contain solutions for a patient to be received intravenously. Flexible containers are typically constructed from two sheets of a polymeric material forming sidewalls that are attached at their outer periphery to define a fluid tight chamber therebetween. In a preferred form of the invention, the fluid container is a coextruded layered structure having a skin layer of a polypropylene and a radio frequency susceptible layer of a polymer blend of 40% by weight polypropylene, 40% by weight of an ultra-low density polyethylene, 10% by weight of a dimer fatty acid polyamide and 10% by weight of a styrene-ethylene-butene-styrene block copolymer. These layered structures are more thoroughly set forth in commonly assigned U.S. Pat. No. 5,686,527 which is incorporated herein by reference and made a part hereof. At one point on the periphery of the container 12 a tubular port 16 is inserted between the sidewalls to provide access to the fluid chamber. A second port 20 is shown for allowing access by a fluid administration set to deliver the reconstituted drug to a patient. However, the first container 12 could be any container, including a syringe barrel, suitable for containing a liquid to be used to reconstitute a drug.

The second container 14, which contains a drug to be reconstituted, is a vial. The vial 14 is typically a glass container with a rubber stopper 22 (FIG. 3) inserted in an opening of the vial 14. The rubber stopper 22 is held in place by an apertured soft metal crimp ring 24, such as aluminum, that is crimped around the stopper 22 and the neck of the vial 14 to fixedly attach it to the vial 14. The device 10 can be adapted to accept vials of any size, particularly 20 mm and 13 mm vials. Additionally, the second container 14 could be any container that is adapted to accommodate drugs that require reconstitution.

Figure 6:
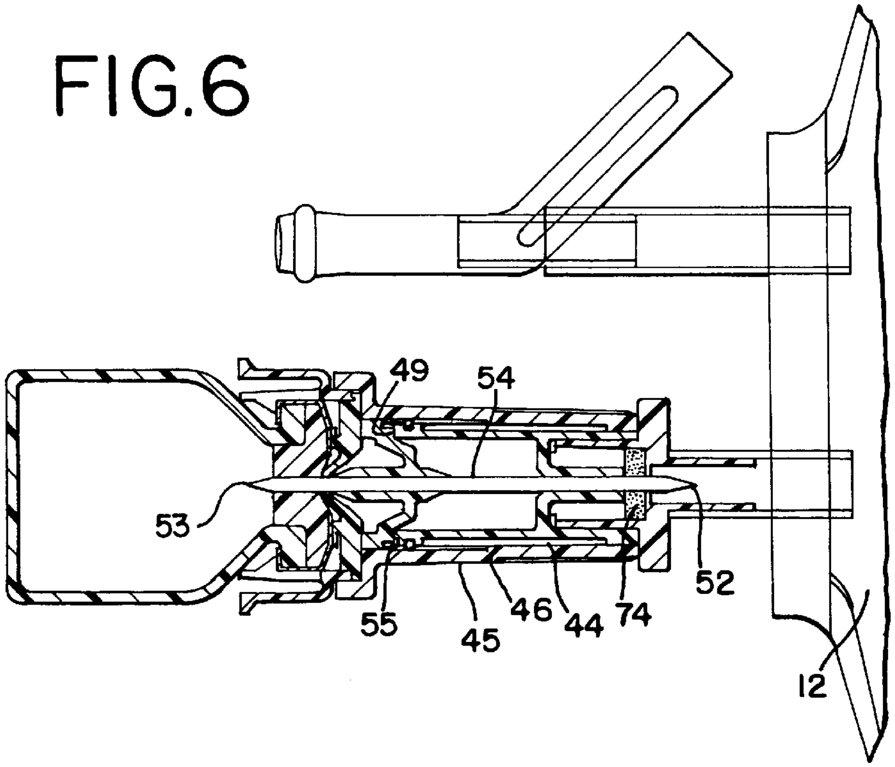
FIG. 6 shows the connector device of FIG. 3 in the activated position.
Figure 7:
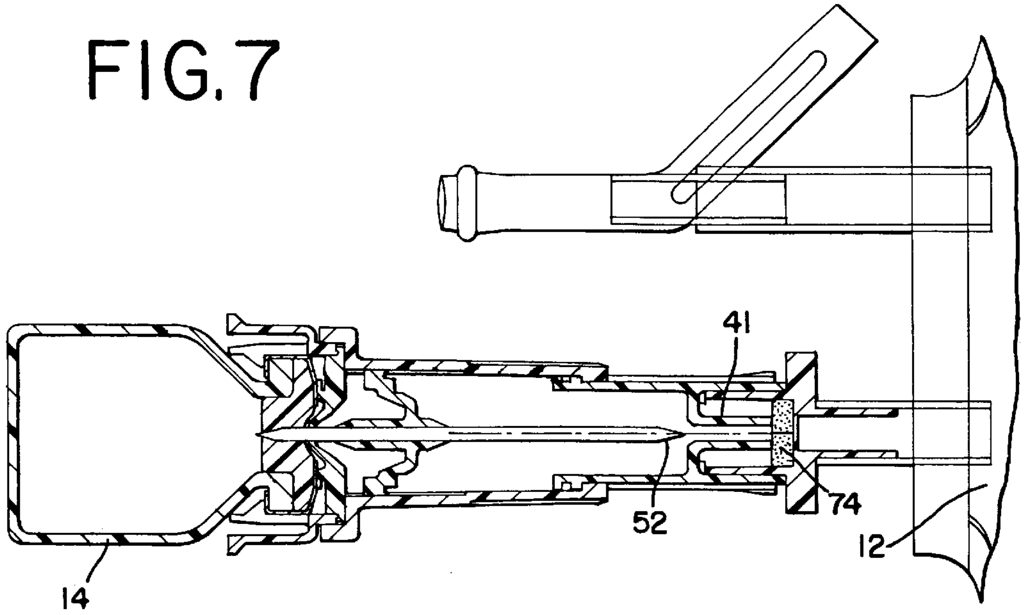
FIG. 7 shows the connector device of FIG. 6 in a deactivated position.

The connector 10, as stated above, is adapted to connect to both the flexible bag 12 and the vial 14 and place the contents of the flexible bag 12 and the vial 14 into fluid communication with one another. As shown in FIG. 1, the connector 10 generally comprises a sleeve assembly 26, a piercing assembly 28 outside the sidewalls of the flexible bag 12, a cup assembly 30 and a port connector 32. As described in greater detail below, the cup assembly 30 and one portion of the sleeve assembly 26 are collectively adapted for axial movement with respect to another portion of the sleeve assembly 26 from an inactivated position (FIGS. 1 and 3) to an activated position (FIG. 6). What is meant by the inactivated position is that the containers 12,14 are not in fluid communication with each other wherein the connector 10 has not been activated. What is meant by the activated position is that the containers 12,14 are placed in fluid communication with each other. What is meant by the deactivated position, or post reconstitution position, is the first container 12 and the second container 14 are not in fluid communication and have been moved from the activated position to the deactivated position (FIG. 7).

As is further shown in FIG. 1, the sleeve assembly 26 generally comprises a first sleeve 33 and a second sleeve 34. The first sleeve 33 and second sleeve 34 are mounted for translational motion with respect to one another from the inactivated position to the activated position. In a preferred form of the invention, the first sleeve 33 is slidably mounted within the second sleeve 34. Each sleeve 33,34 has generally cylindrical walls and collectively the sleeves 33,34 define a central channel 31 through the connector 10. The first sleeve 33 has a first end 35 and a second end 36. The first end 35 is adapted to receive and be connected to the port connector 32. The second end 36 of the first sleeve 33 has an annular groove 39. The annular groove 39 receives a sealing member 40, preferably in the form of an O-ring. The O-ring 40 provides a seal between the first sleeve 33 and the second sleeve 34 and in a preferred form of the invention is disposed between the first sleeve 33 and the second sleeve 34. Of course other sealing members such as gaskets, washers and similar devices could be used to achieve a seal between the sleeves 33,34 as is well known in the art without departing from the present invention. The first sleeve 33 further has a guide 41 at an inner surface of the sleeve 33, intermediate the first end 35 and the second end 36. The guide 41 has an opening 42 adapted to receive and support a portion of the piercing member 28 as will be described in greater detail below.

Figure 2:
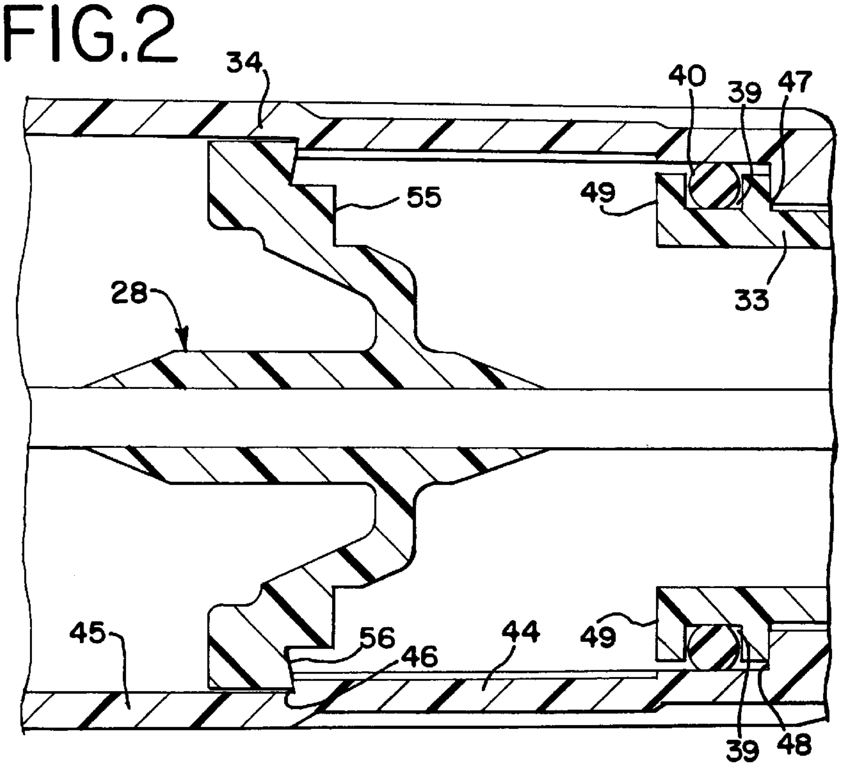
FIG. 2 is an enlarged partial cross-sectional view of the connector device of FIG. 1.

The second sleeve 34 also has a first end 37 and a second end 38. The second end 38 of the second sleeve 34 defines a base 43 that is adapted to connect to the cup assembly 30. The second sleeve 34 accommodates the piercing assembly 28 within the passageway 31. The piercing assembly 28 is slidable within the passageway 31 along an inner surface of the second sleeve 34. Also, as shown in FIG. 2, the second sleeve 34 has a first section 44 and a second section 45. The second section 45 has a larger diameter than the first section 44. At the interface between the first section 44 and the second section 45, a ledge 46 is formed. Finally, the first sleeve 33 has a stop surface 47 that cooperates with a stop surface 48 on the second sleeve 34 that prevent the first sleeve 33 from sliding out of the second sleeve 34. The first sleeve 33 also has a top surface 49 that interfaces with the piercing assembly 28 as will be described in greater detail below.

As further shown in FIG. 1, the piercing assembly 28 generally comprises a hub 50 that supports a piercing member 51. The piercing member 51 has a first end 52 that is positioned within the opening 42 of the guide 41 of the first sleeve 33 when in the inactivated position. A second end 53 of the piercing member is positioned adjacent the cup assembly 30 when in the inactivated position. The piercing member 51, such as a cannula or needle, is a rigid, elongate, spiked member at each end 52,53 having a central fluid passage 54 for establishing a fluid flow passage between the first container 12 and the second container 14. The piercing member is positioned outside the sidewalls of the first container 12 and is mounted thereto. Each end 52,53 of the piercing member 51 terminates in a sharp point or an oblique angle or bevel adapted to pierce through closures as will be described below.

The hub 50, connected to the piercing member 51, is slideable within the passageway 31 along an inner surface of the second sleeve 34. In a preferred form of the invention, the hub 50 has a generally round outer profile and is divided into segments. Preferably, the hub has a greater diameter than the diameter of the first section 44 of the passageway 31 but a smaller diameter than the second section 45. Therefore, the hub 50 must be spring loaded into the first section 44. The spring-loading ensures the O-ring 40 has intimate contact with the first section 44. The piercing member 51 is allowed to move and pierce the closure of the drug vial 14 and pre-slit membrane 74 (described below) adjacent the flexible container 12 when the connector 10 moves from the inactivated position to the activated position. The hub 50 has a stepped configuration. The hub 50 has a first stop surface 55 that cooperates with the top surface 49 of the first sleeve 33. The hub 50 also has a second stop surface 56 that cooperates with the ledge 46 (FIGS. 2 and 6) on the second sleeve 34. The hub 50 further has an annular outer surface 57 that slides along the inner surface of the second sleeve 34. This allows the piercing assembly 28 to "float" within the second sleeve 34.

FIG. 1 further shows the cup assembly 30. The cup assembly 30 is substantially identical to the cup assembly 130 shown in FIGS. 11–16. The cup assembly 30 generally includes a wall portion 58 having a connecting base 59, fingers 60 and a sealing member 61. The cup assembly 30 serves as an attaching member that is adapted to attach the cup assembly 30 to the second container or drug vial 14. The cup assembly 30 has a central opening 62. The wall portion 58 is preferably annular and forms a cup-like shape. The wall portion 58 is preferably continuous and solid. The connecting base 59 of the wall portion 58 is connected to the base 38 of the second sleeve 34. Preferably, the wall portion 58 is connected to the base 38 by ultrasonic bonding. As shown in greater detail in the cup assembly 130 in FIG. 13, the wall portion 172 has bonding ribs (not shown in FIG. 1) which act to focus the ultrasonic bonding energy to the mating surfaces of the second sleeve base 38 and the connecting base 59 to heat and melt the surfaces, therefore, bonding the bases 38,59 together.

The wall portion 58 supports means for fixedly attaching the second container or drug vial 14 to the cup assembly 30. The means shown are a plurality of segmented fingers 60. The fingers 60 are spaced inwardly from the wall portion 72 to allow the fingers 60 to flex when a drug vial 14 is inserted into the cup assembly 30. The fingers 60 are generally trapezoidal in shape and are separated by gaps to define a vial receiving chamber that corresponds to the central opening 62 of the cup assembly 30 for receiving a top of the vial 14. Though the present device utilizes six fingers 60, it can be appreciated by one of ordinary skill in the art that more or fewer fingers could be utilized without departing from the scope of the present invention. For example, eight fingers 60 could be used.

What is meant by "fixedly attached" is that in order to remove the vial 14 from the connector 10, one would have to exert a force considerably in excess of that normally used to operate the device 10. Such a force likely would break, detach or noticeably deform one or more of the segmented fingers 60 or other portions of the connector 10 in the process.

As further shown in FIG. 1, all of the fingers 60 include a flat lead-in section 63, which helps to properly align the vial 14 to be properly aligned with the cup assembly 30. Three of the fingers 60, designated as 60*a*, include, adjacent to the flat lead-in section 63, radially inwardly tapering resilient tabs 64, from a distal end to a proximal end, past which the medical professional must urge a neck of the drug vial 14 in order to connect it to the cup assembly 30. It is appreciated that the tabs 64 are capable of flexing to accommodate varying diameter vial closures. Preferably, the distal end of the fingers 60 have a radiused end that is smooth to avoid cutting the medical personnel handling the connector. The tabs 64 could also be formed, however, as solid bumps without departing from the invention.

As also shown in FIG. 1, the remaining three fingers 60*b* (one shown) have axially extending, standing ribs 65 extending from a generally wedge shaped gusset as disclosed in greater detail in commonly-assigned application Ser. No. 08/986,580 which is incorporated herein by reference and made a part hereof. The gusset spaces the standing ribs 65 from an annular shelf. The front, axially-inward end of the gusset is essentially flush with the annular shelf. The gusset has an upwardly sloping deck from which the standing ribs 92 extend from a central portion thereof. In a preferred form, the standing ribs 65 extend axially-outwardly beyond a distal end of the tabs 64 to assist in aligning the vial 14 with the vial receiving chamber during insertion. The standing ribs 65 are capable of indenting one or more sidewall portions of the metal crimp of the vial 14 in order to inhibit the vial 14 from rotating.

While three fingers 60*a* with resilient tabs 64 and three fingers 60*b* is preferred, providing more or fewer fingers with resilient tabs 64 or ribs 65 would not depart from the scope of the invention. It is also preferable that the fingers 60*a* with the tabs 64 and the fingers 60*b* with the standing ribs 65 are disposed in alternating order. It may also be desirable to place a flexible retraining member, such as shrink wrap or the like, around the fingers 60 to assist in gripping the vial 14.

When the wall portion 58 is connected to the base 38, a space 66 is maintained between a bottom portion of the connecting base 59 and the base 38 of the second sleeve 34. The sealing member 61, preferably in the form of a pierceable septum, is positioned within the space 66. In this embodiment the sealing member 61 and the O-ring 40 hermetically seal the piercing member along its entire length. As will be discussed below, other embodiments of the connector hermetically seal only piercing portions of the piercing member and fluid contacting portions of the piercing members and still achieve a hermetic fluid transfer. The sealing member 61 is positioned adjacent the second end 53 of the piercing member 51. In a preferred embodiment, the sealing member 61 is disk-shaped and has an annular ring 67 that extends axially from the disk and towards the top of the vial 14. The annular ring 67 is dimensioned to tightly and sealingly fit over an aperture of the vial 14 to prevent leakage from the vial 14. The annular ring 67 has an outwardly flaring sidewall 68 that forms a wiper seal with the closure of the vial 14. In addition, the annular ring 67 of the septum 61 is capable of deforming to accommodate dimensional variations in a height of a closure of the second container. The sealing member 61 can be pre-slit at a central location corresponding to the sharp point of the piercing member 52. In an alternative embodiment, the sealing member 61 has a central opening. The central opening receives the piercing member 51 when the connector 10 is moved from its inactivated position to the activated position. The central opening would also allow for steam sterilization past the sealing member 61. Also, the sealing member 61 is lubricated, which lubricates the piercing member 51 allowing it to enter the drug vial 14 more easily. The sealing member 61 is preferably made from Silicone PL-S146.

As further shown in FIG. 1, a seal material 70 is preferably heat sealed to the wall portion 58 and is releasably secured thereto so that it can be peeled away by pulling a tear tab. The wall portion 58 provides for a solid surface to mount the seal material 70 therefore hermitically sealing the connector 10. It is contemplated by the present invention that the seal material could be made of aluminum foil, or of polymeric based material such as TYVEK®, and more preferably TYVEK® grade 1073B , or spun paper or other material that is capable of being peelably attached to the wall portion 58 and capable of providing a barrier to the ingress of contaminants. It is also contemplated that sealing can be accomplished through induction welding or other sealing techniques. In a preferred embodiment, the seal material 70 is made from TYVEK® and is adhesively connected to the wall portion 58. Use of TYVEK® allows for steam to pass therethrough for sterilization purposes and for pressure relief that may be generated in the device during the steam sterilization process.

As further shown in FIG. 1, the port connector 32 has a central base 71 dividing a first portion 72 and a second portion 73. The first portion 72 and the second portion 73 are generally cylindrical. The second portion 73 is connected, preferably by solvent bonding, to an inner surface of the first sleeve 33. Prior to completing this bond, a septum or more preferably a pre-slit rubber membrane, or disk 74, is optionally positioned between the guide 41 of the first sleeve 33 and the central base 71 of the port connector 32. The disk 74 prevents "drip-back" after activation as will be described in greater detail below. The disk 74 prevents fluid from the flexible container 12 from passing into the central passageway 31 without penetration from the piercing member 51. It is also possible to seal the fluid container 12 with a standard membrane in the port tube 16. In this instance it may be preferable to use a plastic piercing member for piercing the membrane. The port connector 32 is then connected to the flexible bag 12 wherein an outer surface of the first portion 72 is connected, preferably by solvent bonding, to an inner surface of the port 16. Typically, the connector 10 is connected to the flexible bag 12 prior to shipping. It will be appreciated by one of ordinary skill in the art, however, that the connector 10 could be connected to the first container 12 at different times.

FIG. 1 shows the connector 10 in its inactivated position where the connector 10 is in its most elongated state wherein the stop surface 47 of the first sleeve 33 abuts the stop surface 48 of the second sleeve 34. FIGS. 3–7 disclose the activation process for the connector 10. As shown in FIG. 3, the seal material 70 is first removed and the drug vial 14 is then inserted into the cup assembly 30 wherein the fingers 60*a* engage the vial 14 to fixedly attach the vial 14 to the connector 10. The annular ring 67 of the sealing member 61 forms a fluid tight seal over the top of the vial 14. Thus, a vial 14 can be selectively attached without piercing the closure 22 of the vial 14. As further shown in FIG. 3, the second end 53 of the piercing member 51 is positioned very close to the sealing member 61 of the cup assembly 30. This reduces the stroke length or distance the piercing member 51 must travel to pierce the closure 22 of the drug vial 14.

Figure 4:
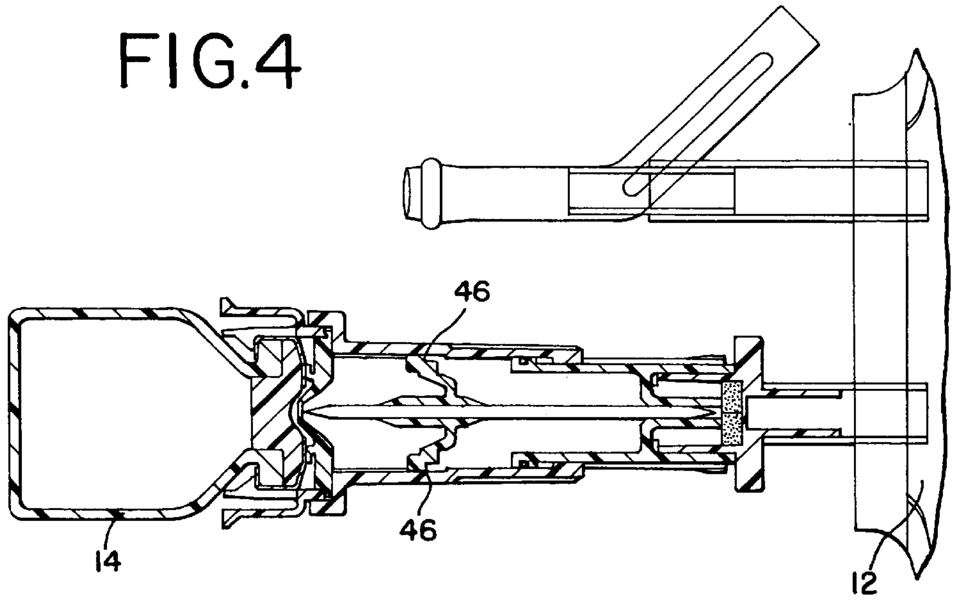
FIG. 4 shows the connector device of FIG. 3 at the initial stages of the activating process.
Figure 5:
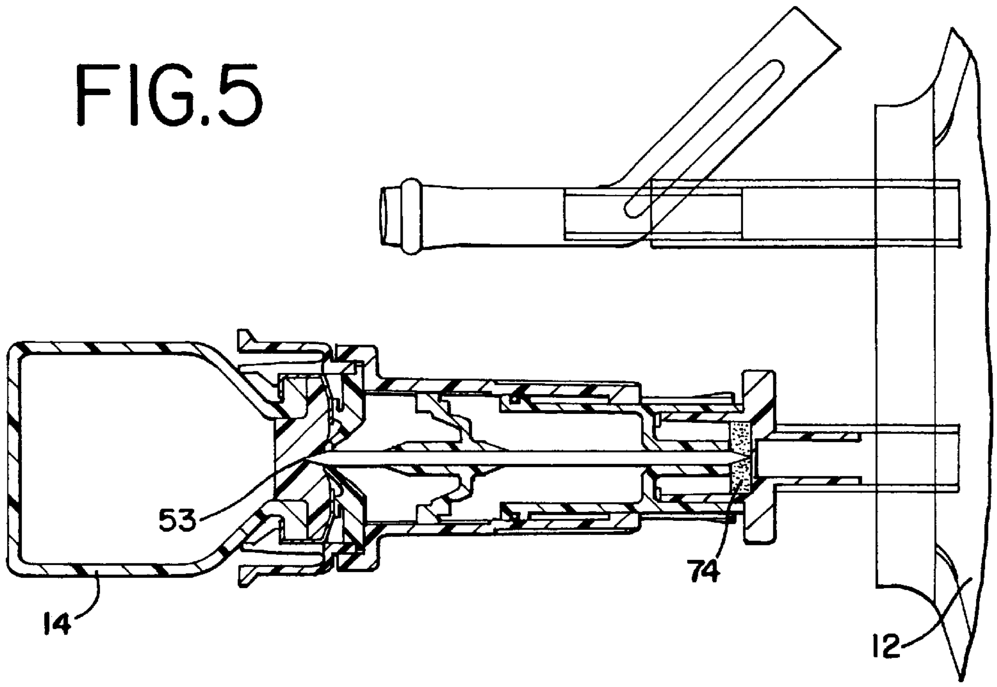
FIG. 5 shows the connector device of FIG. 3 further during the activating process.

As shown in FIG. 4, the first sleeve 33 is rotated relative to the second sleeve 34 to an unlocked position. The vial 14 in the cup assembly 30, along with the second sleeve 34, are moved axially towards the flexible container 12. The second end 53 of the piercing member 51 makes contact with the sealing member 61. As the second sleeve 34 advances further towards the flexible bag 12 (FIG. 5), the second end 53 of the piercing member 51 pierces through the sealing member 61 and into the closure of the vial 14. The second end 53 of the piercing member 51 experiences greater friction as it penetrates the closure of the vial 14. This friction results in the first end 52 of the piercing member 51 to advance towards the flexible container 12 and piercing the rubber disk 74. The guide 41 assures that the first end 42 is properly aligned.

As shown in FIG. 6, as the second sleeve 34 advances further towards the flexible container 12, the top surface 49 of the first sleeve 33 abuts the first stop surface 55 of the hub 50 and advances the hub 50 against the sealing member 61; also, the first end 37 of the second sleeve 34 proceeds to the first end 35 of the first sleeve 33. This position (FIG. 6) represents the activated position. In the activated position, the second end 53 of the piercing member 51 is pierced through the closure 22 of the vial 14, and the first end 52 of the piercing member 51 is pierced through the rubber disk 74. Thus, fluid communication is established between the flexible bag 12 and the vial 14 through the passageway 54 of the piercing member 51.

It is understood that when the connector 10 is in the inactivated position, the central passageway 31 is sealed in a substantially air-tight fashion at one end by the sealing member 61, at an opposite end by the rubber disk 74 and at the interface between the sleeves 33,34 by the O-ring 40. As the vial 14 and second sleeve 34 advance towards the flexible container 12, the volume of the passageway 31 necessarily decreases thus pressurizing the air located in the passageway 31. This pressurized air must be relieved before the connector reaches the final activated position. Accordingly, when the O-ring 40 moves past the first section 44 of the second sleeve 34 to the larger diameter second section 45 of the second sleeve 34, the O-ring no longer contacts the inner surface of the second sleeve 34 (FIG. 6) thus allowing the pressurized air to be relieved.

In the activated position shown in FIG. 6, the diluent contained in the flexible container 12 can pass through the piercing member 51 to reconstitute the drug contained in the vial 14. Once the drug is reconstituted and the resulting mixture passes completely through the piercing member 51 and into the flexible container 12, the drug vial 14 and second sleeve 34 can be pulled back away from the flexible container 12. The second end 53 of the piercing member 51 remains in the closure of the vial 14 and the second end 52 of the piercing member 51 is pulled past the rubber disk 74 (FIG. 7). This position is referred to as the deactivated position, or post reconstitution position. The rubber disk 74 is resilient and seals up thus preventing any of the resulting mixture from dripping back into the drug vial 14.

Figure 8:
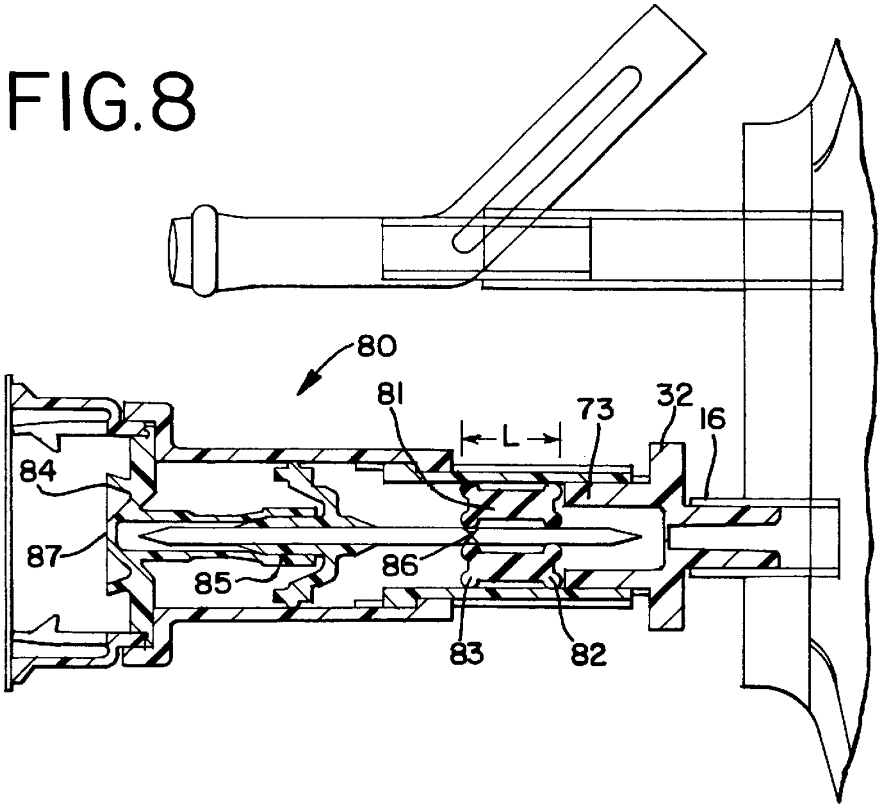
FIG. 8 is a cross-sectional view of another embodiment of a connector device of the present invention, the device being attached to a flexible container and in an inactivated position.

FIG. 8 discloses another embodiment of the connector device of the present invention generally referred to with the reference numeral 80. The connector device 80 is similar to the connector device 10 of FIGS. 1–7. Identical elements will be referred to with identical reference numerals. The connector device 80 does not utilize the rubber disk 74 or guide 41 used in the connector device 10. The connector device 80 does utilize an "x-ring" gasket 81 that seals off the flexible container 12. The gasket 81 is referred to as an "x-ring" gasket or sometimes as an annular "dog-bone" gasket because its cross-sectional shape resembles these shapes. The x-ring gasket 81 has a first end 82 and a second end 83 and supports an end of the piercing member and forms a hermetic seal from its second end 83 to the container. The gasket 81 and the sealing member 84, described below, hermetically seal piercing portions of the piercing member and fluid contacting portions of the piercing member. The x-ring gasket 81 is positioned within the first sleeve 33 wherein its first end 82 is adjacent the second portion 73 of the port connector 32. Thus, the diluent of the flexible container 12 are allowed to travel through the port 16 up but only up to the first end 82 of the x-ring gasket 81. The diluent is allowed to travel through the piercing member 51 but only up to a sealing member 84 as will be described below. The x-ring gasket 81 has a length L that is longer than the distance the piercing member 51 will travel when moving from the inactivated position to the activated position. This ensures that, upon activation, the stroke of the piercing member 51 is such that the mark 86 does not pass beyond the first end 82 of the x-ring gasket 81 towards the flexible container 12. Therefore, only hermetically sealed portions of the piercing member are allowed to pierce the closures of the first and second containers and to contact the fluid being communicated.

The connector 80 also utilizes a sealing member 84 similar to the sealing member 61. The sealing member 84, however, has an elongated sheath 85. The elongated sheath 85 covers and hermetically seals the second end 53 of the piercing member 51. The sealing member 84 has a surface 87 that seals off the diluent in the flexible container 12 until the piercing member 51 pierces the closure of the drug vial 14.

Figure 9:
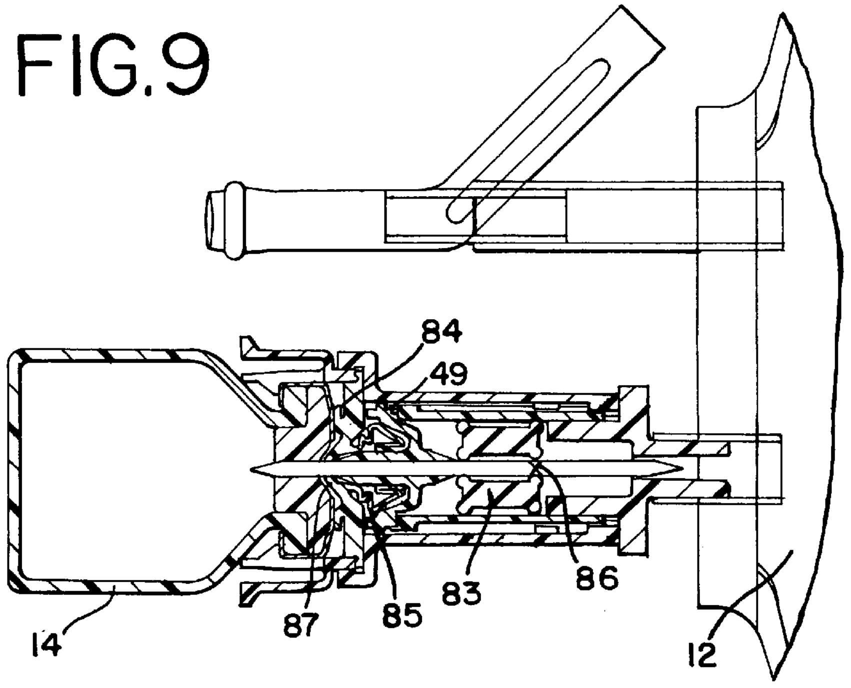
FIG. 9 shows the connector device of FIG. 8 in an activated position.

FIG. 9 shows the connector device 80 in the activated position. Similar to the connector device 10, a single force is applied to the connector 80 to place the connector 80 in the activated position. After the sleeves 33,34 are rotated to an unlocked position, a force is applied to the vial 14 wherein the vial 14 and the second sleeve 34 moves toward the flexible container 12; and the first end 52 of the piercing member 51 moves further past the x-ring gasket 81. The top surface 49 of the first sleeve 33 forces the piercing assembly 28 towards the vial 14 wherein the piercing member 51 pierces the surface 87 of the sealing member 84 and the closure of the vial 14. Thus, fluid communication is established between the flexible bag 12 and the drug vial 14.

Figure 10:
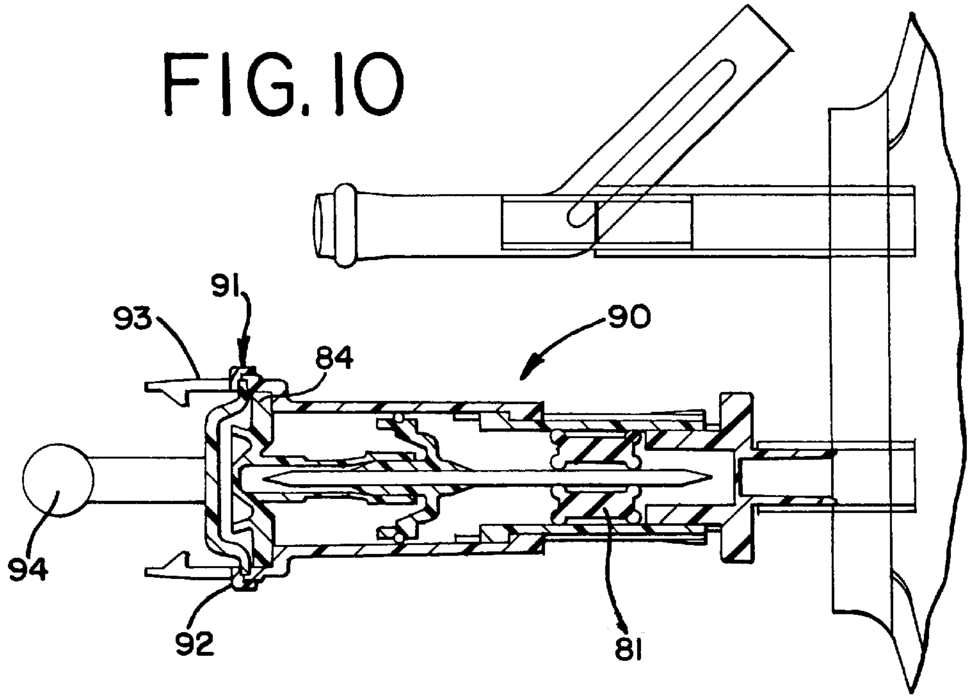
FIG. 10 is a cross-sectional view of another embodiment of a connector device of the present invention, the device being attached to a flexible container and in an inactivated position.

FIG. 10 discloses another embodiment of the connector device of the present invention generally referred to with the reference numeral 90. The connector device 90 is similar to the connector devices 10,80 of FIGS. 1–9. Identical elements will be referred to with identical reference numerals. The connector device 90, however, has a modified cup assembly 91 comprising only a connecting portion 92 and fingers 93. The cup assembly 91 does not have an annular wall portion 58 or the sealing member 70. Rather, a pull-off tab 94 is utilized. The pull-off tab 94 is snap-fitted to the cup assembly 91 adjacent the sealing member 84. When it is desired to reconstitute a drug, the pull-off tab 94 is pulled off and a drug vial 14 is inserted into the cup assembly 91. Activation is accomplished as described above.

Figure 11:
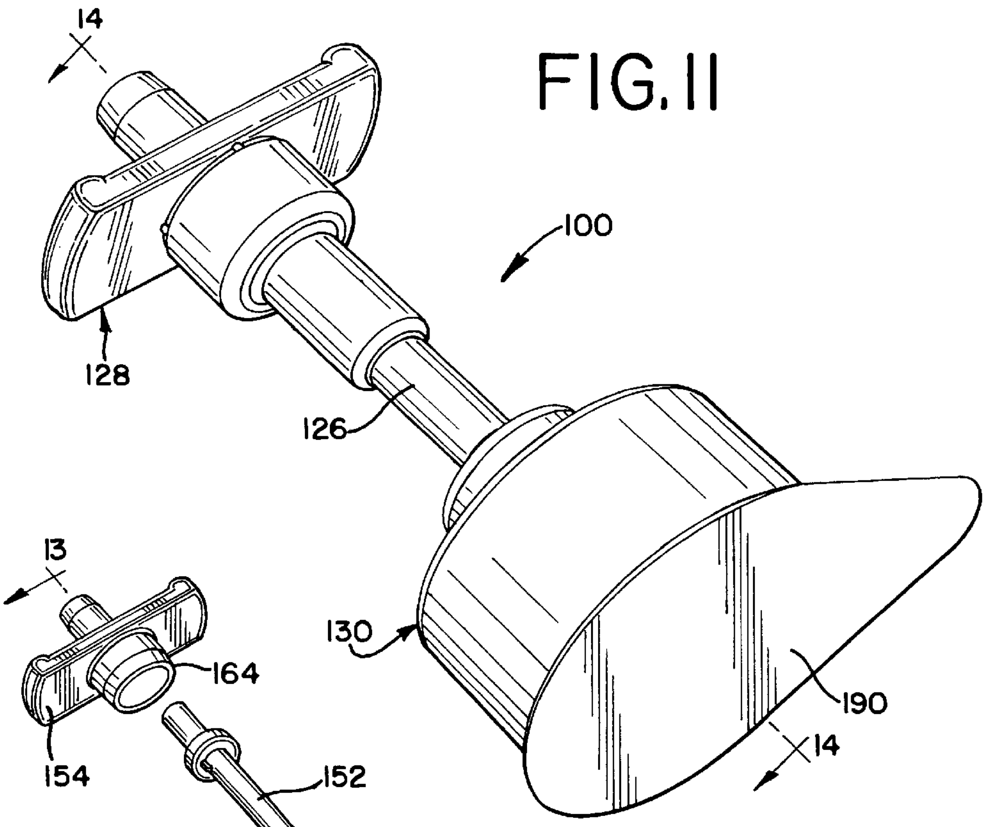
FIG. 11 is a perspective view of another embodiment of a connector device of the present invention.
Figure 12:
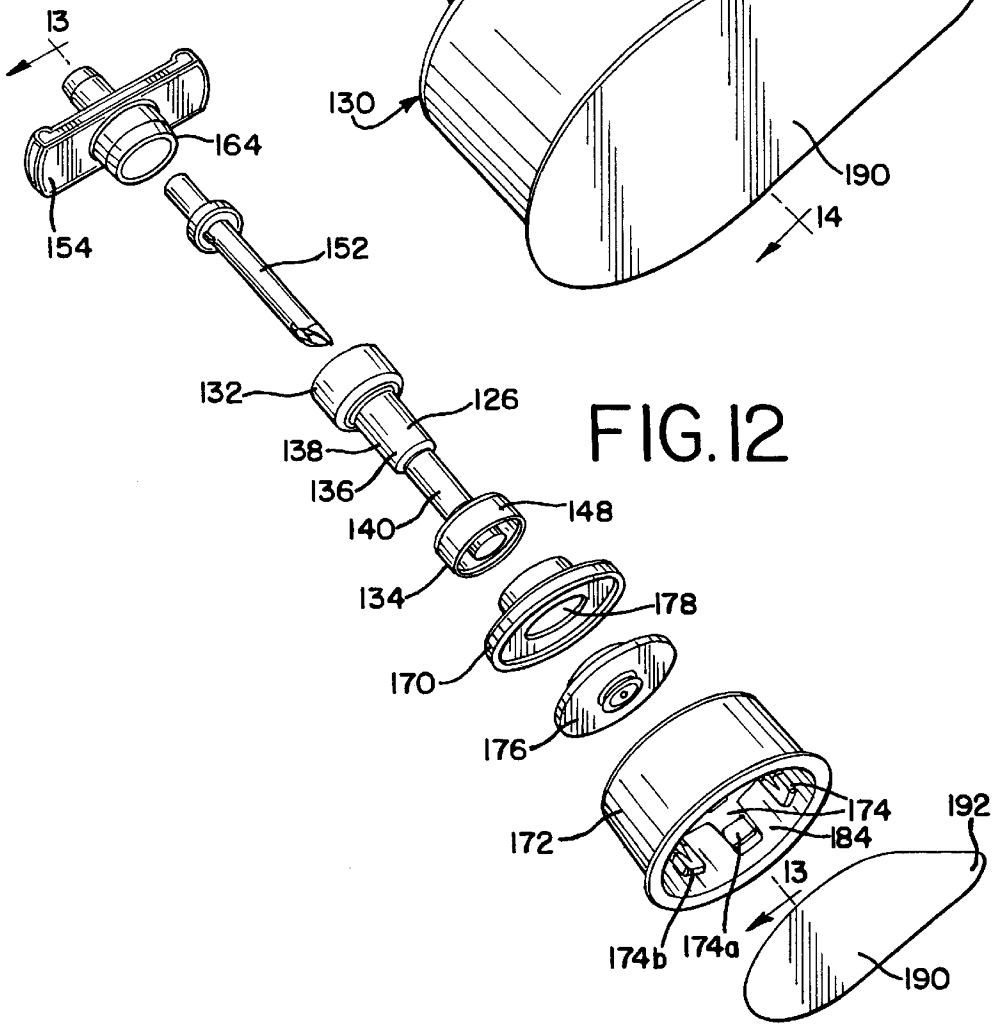
FIG. 12 is an exploded perspective view of the connector device of FIG. 11.
Figure 14:
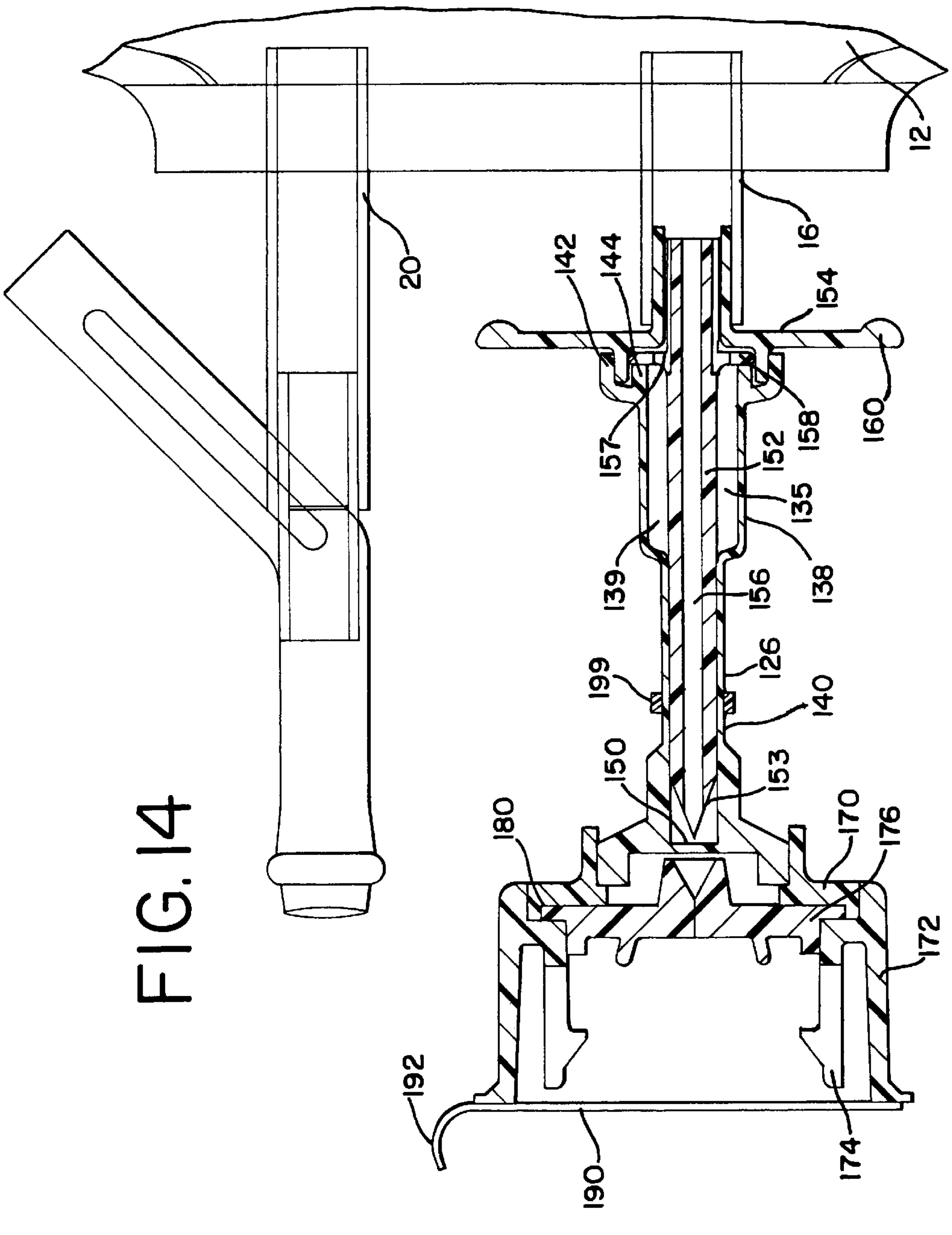
FIG. 14 is cross-sectional view taken along lines 14—14 of FIG. 11 showing the connector device attached to a flexible container.
Figure 15:
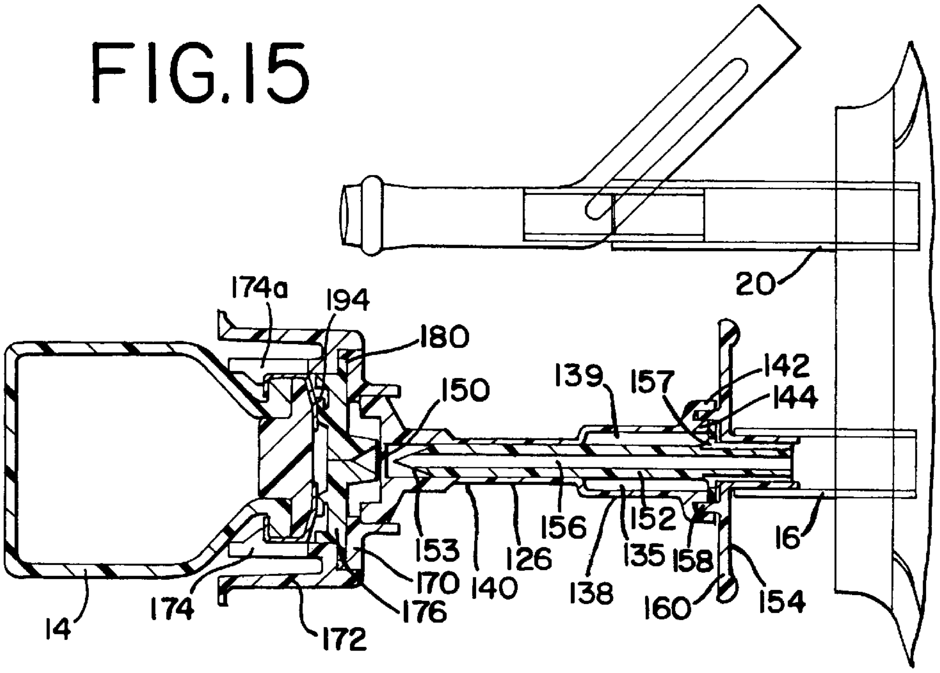
FIG. 15 shows the connector device of FIG. 14 and having a drug vial fixedly secured to the connector device, the connector device being in an inactivated position.
Figure 16:
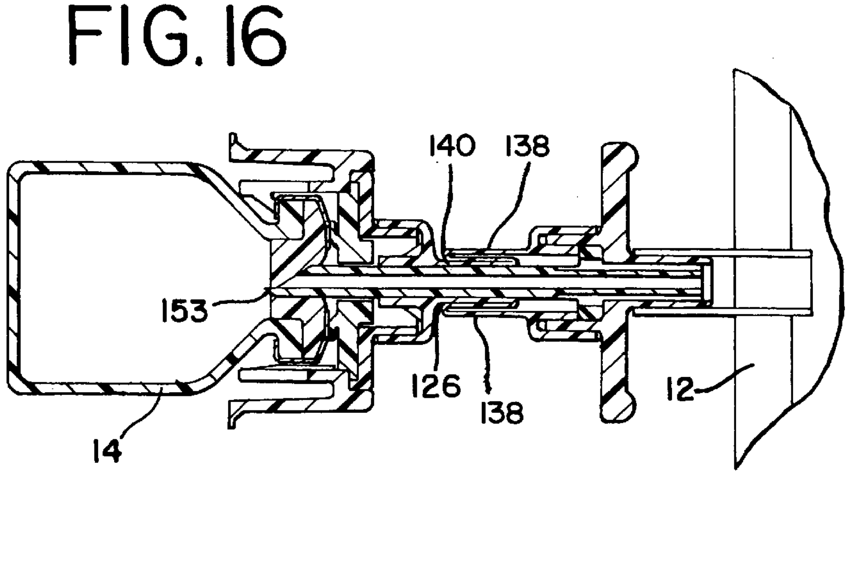
FIG. 16 shows the connector device of FIG. 14 in an activated position.

FIGS. 11–16 disclosed another embodiment of a connector device of the present invention, generally referred to with the reference numeral 100. Similar to the previous embodiments, the connector 100 is adapted to connect to both the flexible bag 12 and the vial 14 and place the contents of the flexible bag 12 and the vial 14 into fluid communication with one another. As shown in FIGS. 11 and 12, the connector 100 generally comprises a sleeve 126, a piercing assembly 128 and a cup assembly 130. The sleeve 126 and cup assembly 130 are adapted for axial movement with respect to the piercing assembly 128 from an inactivated position (FIG. 15) to an activated position (FIG. 16).

Figure 13:
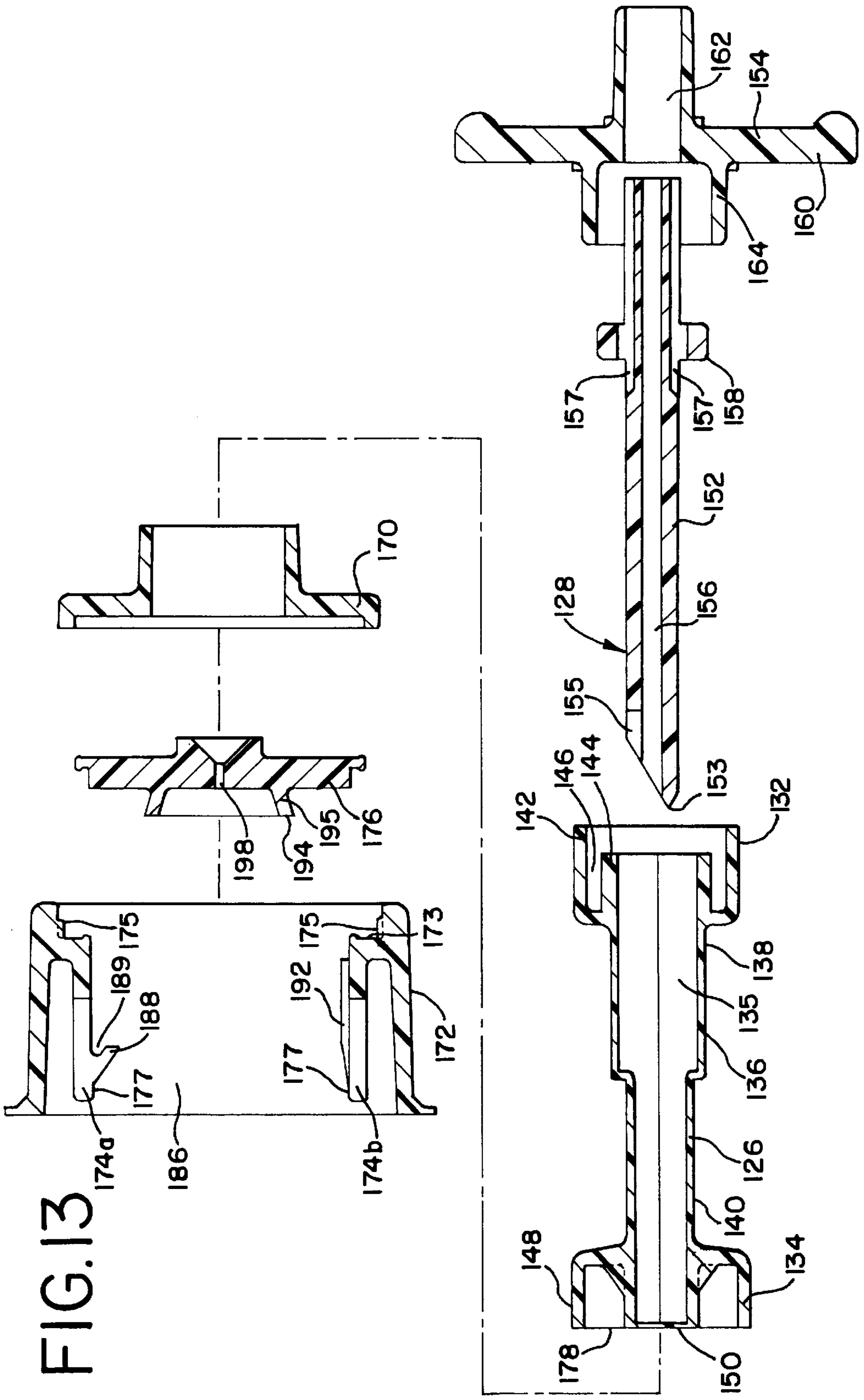
FIG. 13 is an exploded cross-sectional view taken along lines 13—13 of FIG. 12.

As shown in FIGS. 12 and 13, the sleeve 126 has a first end 132 and a second end 134 with an elongate sheath 136 between the ends 132,134 defining a passageway 135. As explained in greater detail below, the sleeve 126 is deformable wherein the sheath 136 can fold onto itself when a force is applied towards the first end 32 along a longitudinal axis of the sleeve 26. The sleeve 126 may sometimes be referred to as a rolling diaphragm because of the way in which it deforms and folds upon itself. To provide the deformability, the sleeve 126 can be made from a flexible material such as a thermoplastic material including PVC and polyolefins.

The sleeve 126 has a first section 138 and a second section 140. The first section 138 has a greater diameter than the second section 140. The first end 132 of the sleeve 126 has a first rim 142 and a second rim 144. The second rim 144 is concentric with, and spaced inward from the first rim 142. An annular slot 146 (FIG. 13) is defined between the rims 142,144. The second end 134 of the sleeve 126 has an annular surface 148 adapted to be connected to the cup assembly 130 as described below. The second end 134 of the sleeve 126 is sealed by a membrane 150. The membrane 150 is formed integral with the sleeve 126 such as by injection molding although it could be separately attached without departing from the scope of the invention. A coining operation is applied to the membrane 150 to reduce the cross-sectional thickness of the membrane 150. This allows the piercing member 128 to more easily pierce the membrane 150.

The piercing assembly 128 generally includes a piercing member 152 connected to a collar 154. The piercing member 152 is connected to the collar 154 in an interference fit although other connections are possible such as by bonding. In addition, the piercing member 152 and collar 154 can be integrally molded in a single piece. It is also understood that the piercing assembly 128 could comprise only the piercing member 152 without the collar 154. The piercing member 152, such as a cannula or needle, is a rigid, elongate, spiked member having a central fluid passage 156 therethrough for establishing a fluid flow passage between the first container 12 and the second container 14. One end of the piercing member 152 terminates in a sharp point 153 or an oblique angle or bevel and is adapted to pierce the rubber stopper 22 of the drug vial 14. In a preferred embodiment, the piercing member 152 is made from polycarbonate PL-2368 but can also be made from other plastics or metal. Also, as shown in FIG. 13, the end of the piercing member 152 ending in the sharp point 153 can have a slot 155 to allow for a larger opening for draining the vial 14 during reconstitution. As shown in FIGS. 13 and 14, the piercing member 152 has radial slots 157 at one end that are spaced from the central fluid flow passage 156. The slots 157 allow for contents of the first container 12 to pass through the slots 157 and into the sleeve 126.

The piercing member 152 has a flange 158 towards one end for contacting the first end 132 of the sleeve 126. The collar 154 serves as a base portion for the connector device 100. The collar 154 has a flange 160 and a central opening 162 through the flange 160. The collar 154 further has an annular ridge 164 extending from the flange 160.

The piercing assembly 128 is connected to the sleeve 126. To this end, the piercing member 152 is positioned within the passageway 135 of the sleeve 126, and specifically within the sheath 136. The collar 154 is connected to the sleeve 126 wherein the annular slot 146 receives the annular ridge 164. Specifically, the annular ridge 164 is solvent bonded to the rims 142,144. The flange 158 of the piercing member 152 is also bonded to the sleeve 126. The solvent bonding in this configuration hermetically seals the sleeve 126 to the collar 154. Solvent bonding is preferable because it is more reliable than other types of connections such as interference fits or threaded connections. In a preferred embodiment, the outer surface of the piercing member 152 is in surface-to-surface contact with an inner surface of the sleeve 126 at the second section 140. Because the first section 138 has a greater diameter than the second section 140, a pocket 139 (FIG. 14) is maintained between the sleeve 126 and piercing member 152 at the first section 138. The pointed end of the piercing member 152 is positioned adjacent the membrane 150.

The outer surface of the collar 154 is adapted to be received in the port 16 of the flexible bag 12. The collar 154 is preferably solvent bonded in the port 16. In such configuration, the piercing member 152 is hermetically sealed at both of its ends. The blunt end is hermetically sealed by the port 16 of the flexible container 12 and the pointed end 153 is hermetically sealed by the membrane 150. In this configuration, and when the connector device 100 is in an inactivated position, contents of the first container 12 can pass from the container 12, through the passageway 156 and up to the membrane 150. The contents can also pass from the container 12, through the radial slots 157 and into the passageway 135 at the first section 138 of the sleeve 126. Specifically, the contents can fill the pocket 139 contacting an inner surface of the sleeve 126. The liquid within the first section 138 provides for greater conduction of the sterilization energy provided when the connector 100 is placed in an autoclave.

FIGS. 12–14 show the cup assembly 130. The cup assembly 130 generally includes a base 170, a wall portion 172, fingers 174 and a sealing member 176. The cup assembly 130 serves as an attaching member that is adapted to attach the assembly 130 to the second container or drug vial 14. The base 170 is disk-shaped having a center opening 178 therethrough. The wall portion 172 is preferably annular and is connected to an outer periphery of the base 170 forming a cuplike shape. The wall portion 172 is preferably continuous and solid. Preferably, the wall portion 172 is connected to the base 170 by ultrasonic bonding. As shown in FIG. 13, the wall portion 172 has bonding ribs 175 which act to focus the ultrasonic bonding energy to the mating surfaces of the base 170 and the wall portion 172 to heat and melt the surfaces, therefore, bonding the base 170 and wall portion 172 together. This two-piece assembly, along with the sealing member 176 act to prevent microbes from contaminating the connector 100. Also, a flash trap is provided between the base 170 and wall portion 172 to catch material from the ultrasonic bonding.

The cup assembly 130 is attached to the second end 134 of the sleeve 126. Specifically, the base 170 is solvent bonded to the second end 134 of the sleeve 126. This connection requires bonding a polycarbonate material (base 170) to a vinyl material (sheath 126). Because this particular connection is not considered a solution contact, the bonding agent used is typically methyl-ethyl-ketone (MEK). In a solution contact, such as the connection between the collar 154 and the port 16 of the flexible container 12, and the connection between the collar 154 and the sheath 126, the bonding agent used is typically cyclo-hexanol. MEK is not typically used on solution contacting surfaces.

The wall portion 172 supports means for fixedly attaching the second container or drug vial 14 to the cup assembly 130. The means shown are a plurality of segmented fingers 174 (FIGS. 12 and 13). The fingers 174 are spaced inwardly from the wall portion 172 to allow the fingers 174 to flex when a drug vial 14 is inserted into the cup assembly 130. The fingers 174 are generally trapezoidal in shape and are separated by gaps 184 (FIG. 11) to define a vial receiving chamber 186 for receiving a top of the vial 14. Though the present device utilizes six fingers 174, it can be appreciated by one of ordinary skill in the art that more or fewer fingers could be utilized without departing from the scope of the present invention.

What is meant by “fixedly attached” is that in order to remove the vial 14 from the connector 100, one would have to exert a force considerably in excess of that normally used to operate the device 100. Such a force likely would break, detach or noticeably deform one or more of the segmented fingers 174 or other portions of the connector 100 in the process.

As shown in FIG. 13, all of the fingers 174 include a flat lead-in section 177, which helps to properly align the vial 14 to be properly aligned with the cup assembly 130. Three of the fingers 174, designated as 174*a,* include, adjacent to the flat lead-in section 177, radially inwardly tapering resilient tabs 188, from a distal end to a proximal end, past which the medical professional must urge a neck of the drug vial 14 in order to connect it to the cup assembly 130. It is appreciated that the tabs 188 are capable of flexing to accommodate varying diameter vial closures. Preferably, the distal end of the fingers 174 have a radiused end that is smooth to avoid cutting the medical personnel handling the connector. The tabs 188 shown have a space 189 between the distal end of the tab and the finger 174. The tabs 188 could also be formed, however, as solid bumps without departing from the invention.

As shown in FIG. 13, the remaining three fingers 174*b* have axially extending, standing ribs 192 extending from a generally wedge shaped gusset as disclosed in greater detail in commonly-assigned application Ser. No. 08/986,580. The gusset spaces the standing ribs 192 from the annular shelf 197. The front, axially-inward end of the gusset is essentially flush with the annular shelf. The gusset has an upwardly sloping deck from which the standing ribs 192 extend from a central portion thereof. In a preferred form, the standing ribs 192 extend axially-outwardly beyond a distal end of the tabs 188 to assist in aligning the vial 14 with the vial receiving chamber during insertion. The standing ribs 192 are capable of indenting one or more sidewall portions of the metal crimp of the vial 14 in order to inhibit the vial 14 from rotating.

While three fingers 174*a* with resilient tabs 188 and three fingers 174*b* is preferred, providing more or fewer fingers with resilient tabs 188 or ribs 192 would not depart from the scope of the invention. It is also preferable that the fingers 174*a* with the tabs 188 and the fingers 174*b* with the standing ribs are disposed in alternating order. It may also be desirable to place a flexible retraining member, such as shrink wrap or the like, around the fingers 174 to assist in gripping the vial 14.

When the wall portion 172 is connected to the base portion 170, a space 180 is maintained between a bottom portion 173 of each finger 174 and the base portion 170. The sealing member 176, preferably in the form of a pierceable septum, is positioned within the space 180. The sealing member 176 covers the center opening 178 and is adjacent to the membrane 150. In a preferred embodiment, the sealing member 176 is disk-shaped and has an annular ring 194 that extends axially from the disk and towards the top of the vial 14. The annular ring 194 is dimensioned to tightly and sealingly fit over an aperture of the vial 14 to prevent leakage from the vial 14. The annular ridge 194 has an outwardly flaring sidewall 195 that forms a wiper seal with the closure of the vial 14. In addition, the annular ring 194 of the septum 176 is capable of deforming to accommodate dimensional variations in a height of a closure of the second container. The sealing member 176, for all embodiments, can be a solid septum or a pre-slit septum, or a septum having a portion removed to define a central opening 198 corresponding to the sharp point of the piercing member 152. Most preferably the sealing member 176 has the central opening 198. The central opening 198 receives the piercing member 152 when the sleeve 126 is moved from its inactivated position to the activated position. The central opening 198 also allows for steam sterilization past the sealing member 176. Also, the sealing member 176 is lubricated, which lubricates the piercing member 152 allowing it to enter the drug vial 14 more easily. The sealing member 176 is preferably made from Silicone PL-S146.

As shown in FIGS. 11, 12 and 14, a seal material 90 is preferably heat sealed to the wall portion 172 and is releasably secured thereto so that it can be peeled away by pulling a tear tab 192. The wall portion 172 provides for a solid surface to mount the seal 190 therefore hermitically sealing the connector 100. It is contemplated by the present invention that the seal could be made of aluminum foil, or of polymeric based material such as TYVEK®, or spun paper or other material that is capable of being peelably attached to the wall portion 172 and capable of providing a barrier to the ingress of contaminants. It is also contemplated that sealing can be accomplished through induction welding or other sealing techniques. In a preferred embodiment, the seal material 190 is made from TYVEK® and is adhesively connected to the wall portion 172. Use of TYVEK® allows for steam to pass therethrough for sterilization purposes.

As shown in FIG. 14, the connector 100 may include a slip ring 99 to prevent inadvertent actuation. The slip ring 199 is tightly wrapped around the sleeve 126 preventing movement of the sleeve 126 with respect to the piercing member 152. The slip ring 199 is frangibly attached around the sleeve 126 allowing for easy removal prior to activation of the connector 100.

FIG. 14 shows the connector 100 in its inactivated position where the sleeve 126 is in a general elongated state. As previously stated, the connector 100 is adapted to be connected to the first container 12. The outer surface of the collar 154 is bonded to the inner surface of the port 16. It will be appreciated by one of ordinary skill in the art that the connector 10 could be connected to the first container 12 at different times. As shown in FIG. 15, the seal 190 is removed and the drug vial 14 is then inserted into the cup assembly 130 wherein the fingers 174*a* engage the vial 14 to fixedly attach the vial 14 to the connector 100. The annular ring 194 of the sealing member 176 forms a fluid tight seal over the top of the vial 14.

As shown in FIG. 16, to place the connector 100 in an activated position, the slip ring 100, if utilized on the connector 100, is removed. A medical professional then pushes the drug vial 14 towards the flexible bag 12. The sheath 136 of the deformable sleeve 126 rolls and folds over itself. Thus, the second section 140 slides along the piercing member 152 in frictional engagement and the first section 138 folds over the second section 140 making the sheath 136 approximately half its original length. The piercing member 152 pierces through the membrane 150, passes through the central opening 197 of the sealing member 176 and the rubber stopper 122 of the vial 14. Thus, the flexible bag 12 is placed in fluid communication with the drug vial 14.

Once the rubber stopper 22 is punctured, the first container 12 and the second container 14 are in fluid communication. The medical professional will then squeeze the flexible bag 12 to force the fluid into the vial 14 to reconstitute the drug, shaking the vial 14 as necessary to facilitate reconstitution, and inverting the vial 14 in relation to the bag 12 to allow the reconstituted drug to flow back into the bag 12.

In the configuration of the present invention, the sleeve 126 encapsulates the piercing member 152. In addition, the membrane 150 encloses one end of the piercing member 152 and the first container 12 encloses the other end of the piercing member 152. Accordingly, the piercing member 152 is independently hermetically sealed. The sleeve 126 is rigid enough to support the cup assembly 130 and attached drug vial 14. The sleeve 126, however, is also flexible enough to deform and fold upon itself to allow for easy insertion of the piercing member 152 into the drug vial 14. This configuration also provides ready visual determination if the connector 10 has been activated. The seal 190 also is tamper evident. Also with this configuration, the integrity of the drug vial is maintained until the connector 100 is moved to its activated position.

It can be appreciated that certain steps of this method of reconstituting a drug may be unnecessary if the device is received preattached to the fluid container or preattached to both the vial and the flexible container. In a preferred embodiment, the connector 100 will be preattached to the flexible container 12 and the drug vial 14 will be separately packaged.

Nevertheless, it is possible to preattach the vial 14 to the connector 100 for shipment. Preattaching the vial 14 to the connector 100 may be accomplished using aseptic connecting techniques. The preferred method of preattaching the device 100 to the vial 14 include the steps of: 1) positioning the vial 14 and the cup assembly 130 into opposed relationship, 2) simultaneously bringing the segmented fingers 174 into operative engagement with the vial 14 while sterilizing the connection by exposing the connecting portions of the device 100 and the vial 14 with, preferably, gamma sterilization or other sterilization energies or techniques. These steps can be carried out manually by medical personnel or automatically by a machine. The preattached vial 14 and connector 100 may be wrapped in an over pouch for shipping and storage. An over pouch, however, is typically not used with the connector 100 thus saving in material costs.

Figure 17:
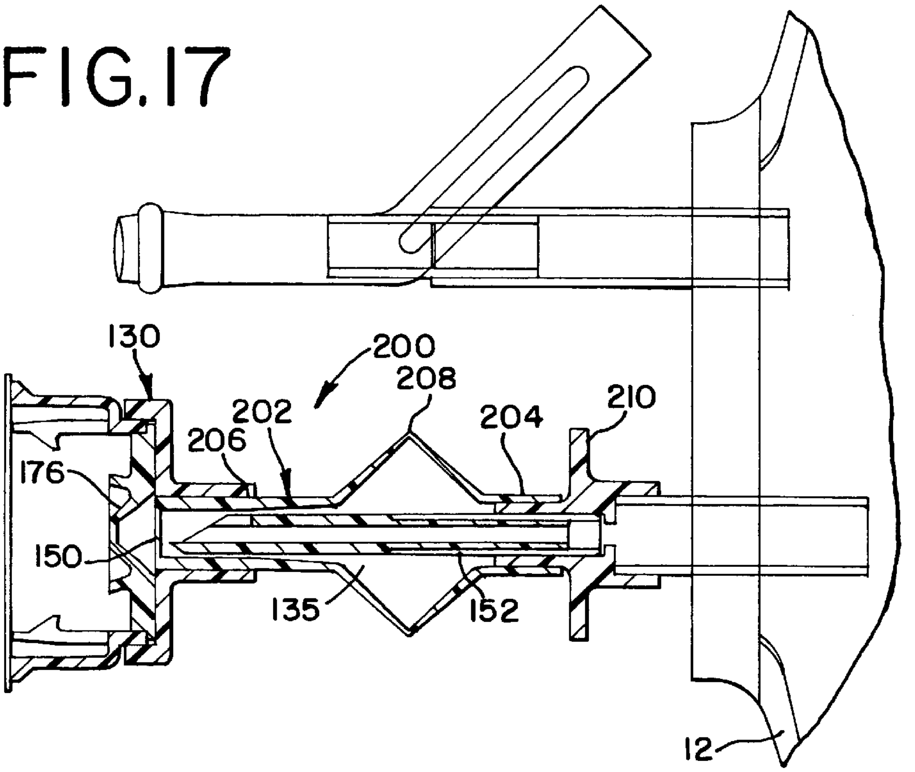
FIG. 17 is cross-sectional view is a cross-sectional view of another embodiment of a connector device of the present invention, the device being attached to a flexible container and in an inactivated position.
Figure 18:
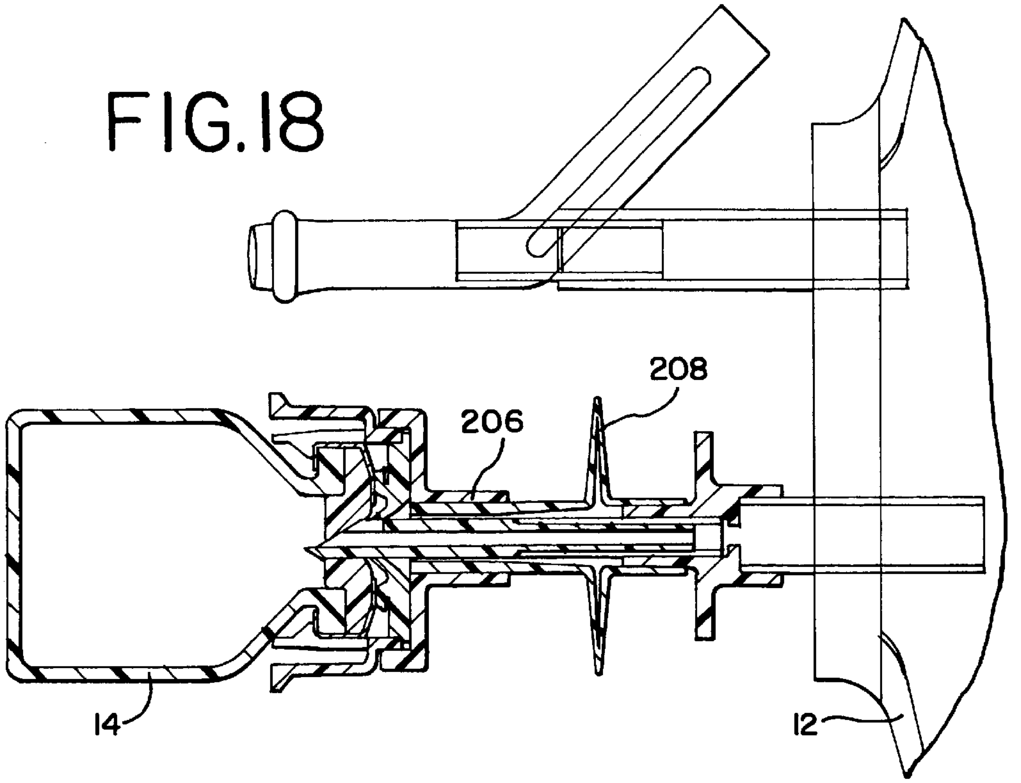
FIG. 18 shows the connector device of FIG. 17 with a drug vial attached and in an activated position.

FIGS. 17 and 18 disclose another embodiment of the connector device of the present invention generally referred to with the reference numeral 200. The connector device 200 of FIGS. 17 and 18 is similar to the connector device 100 of FIGS. 11–16 and identical elements will be referred to with identical reference numerals. Rather than using the rolling diaphragm sleeve 26, the connector device utilizes a deformable bellows assembly 202. The bellows assembly 202 is preferably made of a vinyl material. The bellows assembly 202 has a first end 204 and a second end 206 having a bellows portion 208 therebetween. The first end 204 is connected to the collar 154 of the piercing assembly 128. The second end 206 is connected to the cup assembly 130. As with the connector device 100, diluent from the flexible container 12 can pass through the piercing member 152 and into the passageway 135.

FIG. 18 shows the connector device 200 in the activated position. The activation process is similar to that described above. As the vial 14 is advanced towards the flexible bag 12, the second end 206 of the bellows assembly 202 slides along the piercing member 152, and the bellows portion 208 folds in accordion-like fashion. The piercing member 152 pierces through the membrane 150 and septum 176 and into the closure of the vial 14, thus establishing fluid communication between the flexible bag 12 and the vial 14.

Figure 19:
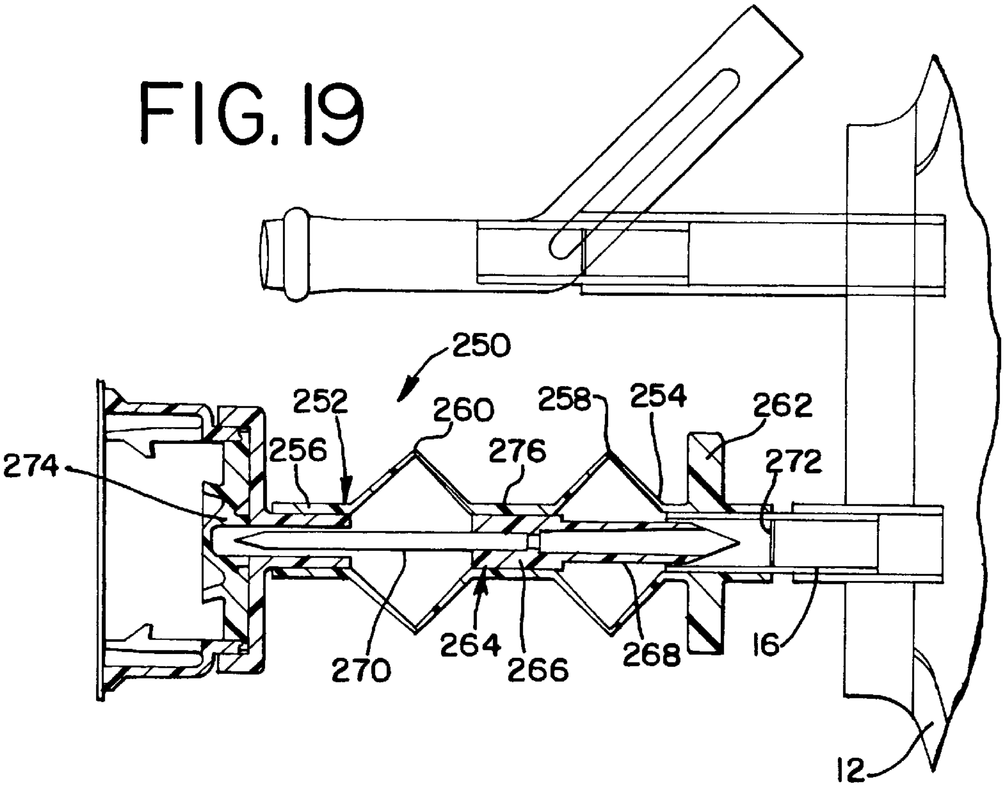
FIG. 19 is a cross-sectional view of another embodiment of a connector device of the present invention, the device being attached to a flexible container and in an inactivated position; and, FIG. 20 shows the connector device of FIG. 18 with a drug vial attached and in an activated position.
Figure 20:
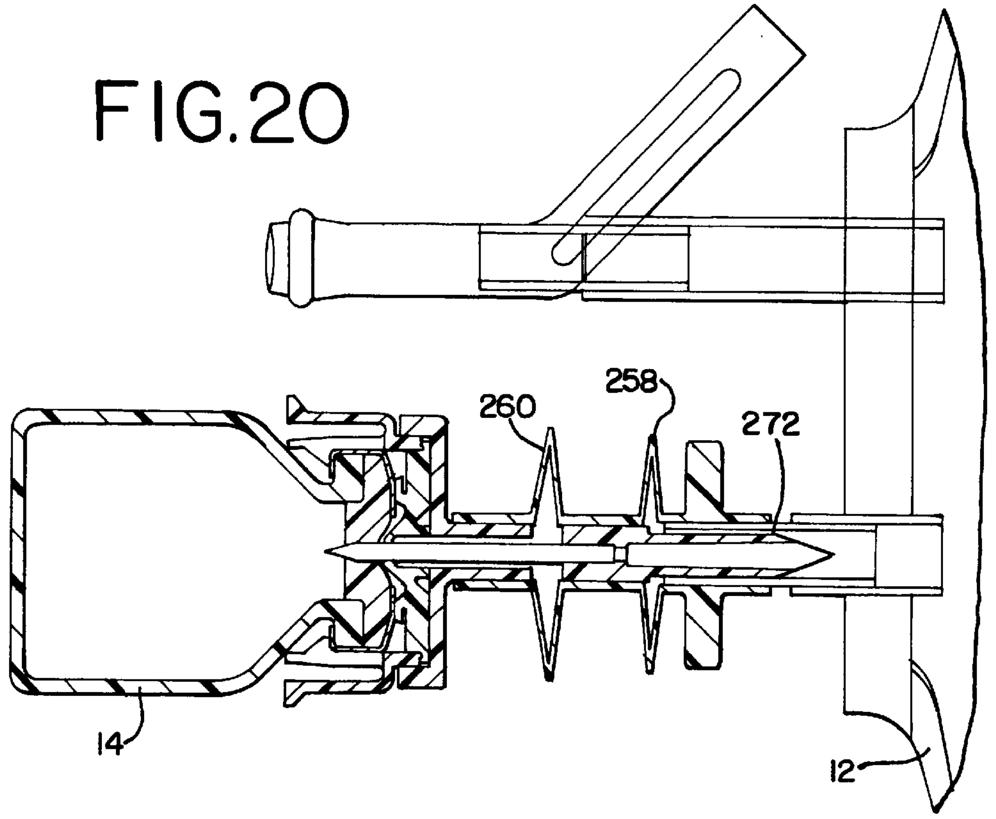

FIGS. 19 and 20 disclose yet another embodiment of the connector device of the present invention generally referred to with the reference numeral 250. This connector device 250 of FIGS. 19 and 20 is similar to the connector devices 200 of FIGS. 17 and 18 and FIGS. 11–16 and identical elements will be referred to with identical reference numerals. The connector device 250 utilizes a deformable bellows assembly 252, preferably made of a vinyl material. The bellows assembly 252 has a first end 254 and a second end 256 having a first bellows portion 258 and a second bellows portion 260 therebetween. The first end 254 is connected to a port connector 262. The port connector 262 is connected to the port 16 of the flexible container 12. The second end 256 is connected to the cup assembly 130. As further shown in FIG. 19, the connector device 250 utilizes a different type of piercing assembly 264. The piercing assembly 264 generally comprises a hub 266, a first piercing member 268 and a second piercing member 270. The first piercing member 268 is preferably made of polycarbonate and is adapted to pierce a membrane 272 that seals the flexible container 12. The second piercing member 270 is preferably made of metal and is adapted to pierce a sealing member 274 and a closure of the vial 14. The first and second piercing members 268,270 are overmolded into the hub 266. As further shown in FIG. 19, the hub 264 is connected to an intermediate portion 276 of the bellows assembly 252 between the first bellows portion 258 and the second bellows portion 260. This connection is preferably a solvent bond. Thus, the piercing assembly 264 is fixedly secured to the bellows assembly 252 and therefore moves therewith.

FIG. 20 shows the connector device 250 in the activated position. The activation process is similar to that described above. As the vial 14 is advanced towards the flexible container 12, the second bellows portion 260 folds in accordion-like fashion wherein the second piercing member 270 pierces through the sealing member 274 and closure of the vial 14. Also, the first bellows portion 254 folds in accordion-like fashion wherein the first piercing member 268 pierces through the membrane 272. Accordingly, fluid communication is established between the flexible container 12 and the vial 14 via the piercing assembly 264. Because the piercing assembly 264 is fixedly attached to the bellows assembly 252, the second piercing member 270 can be withdrawn from the vial 14 and the first piercing member 268 can be withdrawn from the port 16. The sealing member 176 will seal itself thus preventing any drip-back from the flexible container after reconstitution is complete. With the connector device 250 of FIGS. 19 and 20, diluent from the flexible container 12 is prevented from contacting the surface of the bellows assembly 252. The use of the two bellows portions 258,260 provides dual control. The operator of the device can pierce the vial 14 before the flexible bag 12 or vice-versa.

The connector devices of the present invention can be sterilized by known procedures such as steam sterilization or radiation sterilization. Also, it is understood the any of the features of the different embodiments of the connector devices described above can be combined or eliminated as desired. It should also be understood that each of the devices of the present invention allow for pre-attaching a vial to the connector and shrink wrapping the two to provide a tamper evident feature.

While the specific embodiments have been illustrated and described, numerous modifications come to mind without significantly departing from the spirit of the invention, and the scope of protection is only limited by the scope of the accompanying claim.

We claim:

1. A connector device for establishing fluid communication between a liquid container having sidewalls and a drug vial having a neck with a closure therein, the connector comprising:

a piercing member having a first end and a second end and a central fluid pathway, the piercing member being mounted to the liquid container and having fluid accessing portions hermetically sealed from an outside environment;

a vial receiving chamber associated with the piercing member and being dimensioned to connect to the vial and wherein the vial may be selectively attached to the device without piercing the closure of the vial and without breaching the hermetic seal of the fluid accessing portions of the piercing member;

means for connecting the vial receiving chamber to the liquid container; and wherein the device is movable from an inactivated position where the piercing member is outside the sidewalls and no fluid flows between the liquid container and the drug vial, to an activated position wherein fluid flows through the fluid pathway between the liquid container and the drug vial, the device being movable from the inactivated position to the activated position by a force applied to the device outside the liquid container.

2. The device of claim 1 wherein the means for connecting the vial receiving chamber to the liquid container comprises:

a first sleeve and a second sleeve mounted for translational motion with respect to one another, the first sleeve being connected to the liquid container and the second sleeve being connected to the vial receiving chamber.

3. The device of claim 2 wherein the first sleeve is mounted within the second sleeve.

4. The device of claim 3 wherein the second sleeve slidably mounts the piercing member for translational motion.

5. The device of claim 4 wherein the second sleeve has an inner surface and the piercing member is capable of sliding on the inner surface.

6. The device of claim 5 wherein a hub mounts the piercing member inside the second sleeve.

7. The device of claim 2 further comprising means disposed between the first sleeve member and the second sleeve member for sealing the first sleeve member and the second sleeve member.

8. The device of claim 1 wherein the means for connecting the vial receiving chamber to the liquid container comprises:

a flexible sleeve having a first end and a second end and defining a central passageway;

the piercing member being positioned within the passageway; and the sleeve being slidable with respect to the piercing member from the inactivated position to the activated position wherein the sleeve slides along the piercing member and folds upon itself, the piercing member piercing a closure of the vial establishing fluid communication between the liquid container and the vial.

9. The device of claim 8 wherein the sleeve has a first section and a second section, the first section having a greater diameter than the second section, wherein when the sleeve moves from the inactivated position to the activated position, the second section slides along the piercing member and the first section folds upon the second section.

10. The device of claim 8 wherein the vial receiving chamber comprises a base connected to a wall portion, the wall portion having a plurality of fingers inwardly spaced from the wall portion and adapted to cooperatively receive the vial, the base being connected to the sleeve.

11. The device of claim 10 further comprising a sealing member positioned between a bottom portion of each finger and the base.

12. The device of claim 11 wherein the sealing member is a pierceable septum.

13. The device of claim 12 wherein the septum comprises a disk, the piercing member passes through the disk when the sleeve is moved from the inactivated position to the activated position.

14. The device of claim 13 wherein the disk further has a generally centrally disposed annular ring extending axially from the disk, the annular ring being dimensioned to fit over a closure of the container.

15. The device of claim 12 wherein the septum is capable of deforming to accommodate dimensional variations in a height of the closure of the vial.

16. The device of claim 8 wherein the piercing member has a radial slot spaced from the fluid flow passage allowing contents of the liquid container to pass through the radial slot and into contact with an inner surface of the sleeve.

17. A connector device for establishing fluid communication between a liquid container and a vial container comprising:

a first sleeve and a second sleeve mounted for translational movement with respect to one another and define a central channel therein, the first sleeve and the second sleeve each having an inner surface, the second sleeve is adapted to attach to the vial and, the first sleeve is mounted within the second sleeve and adapted to attach to the liquid container;

a piercing member having opposed piercing ends, the piercing member being mounted in the central channel;

means for hermetically sealing the piercing ends when the device is connected to the first container and the second container;

a vial receiving chamber on the second sleeve and being dimensioned to connect to the vial and wherein the vial may be selectively attached to the device without piercing the closure of the vial and without breaching the hermetic seal of the piercing ends; and the first sleeve and the second sleeve are capable of being moved from an inactivated position where fluid cannot flow through the device to an activated position where fluid can flow through the device, the device is capable of being moved from the inactivated position to the activated position by applying a force to the device outside the first container and the second container.

18. The device of claim 17 wherein the means for hermetically sealing comprises a sealing member disposed between the first sleeve and the second sleeve.

19. The device of claim 18 wherein the sealing member is mounted on the first member and slides along the inner surface of the second sleeve.

20. The device of claim 19 wherein the means for sealing further comprises a septum mounted within the vial receiving chamber to seal the second sleeve.

21. The device of claim 20 further comprising means for venting the device when the device is moved from the inactivated position to the activated position.

22. The device of claim 21 wherein the means for venting comprises an increased inner diameter portion of the second sleeve proximate a distal end of the second sleeve and upon which the sealing member does not seal.

23. The device of claim 19 further comprising means for supporting the piercing member within the central channel.

24. The device of claim 23 wherein the means for supporting comprises a hub mounting the piercing member, a portion of the hub slides on the inner surface of the second sleeve.

25. The device of claim 24 wherein the hub mounts the piercing member along a generally central portion of the piercing member.

26. The device of claim 24 wherein the means for mounting the piercing member further comprises a guide within the first sleeve that supports a portion of the piercing member.

27. The device of claim 26 wherein the guide is positioned adjacent the liquid container.

28. The device of claim 26 further comprising a disk positioned between the liquid container and the guide.

29. The device of claim 28 wherein when the device is in the activated position the piercing member punctures the septum.

30. The device of claim 29 wherein the device is capable of being positioned between an activated position and a deactivated position wherein in the deactivated position the first end of the piercing member is pulled out of the disk and guide.

31. The device of claim 17 wherein the means for hermetically sealing comprises a first means for sealing the first sleeve and a second means for sealing the second sleeve.

32. The device of claim 31 wherein the first sealing means comprises an annular gasket positioned in the first sleeve.

33. The device of claim 32 wherein the annular gasket supports a portion of the piercing member.

34. The device of claim 33 wherein the piercing member travels a distance when the device is moved from the inactivated position to the activated position and wherein the annular gasket has a length that is greater than the distance.

35. The device of claim 34 wherein the annular gasket has an X-shaped cross section.

36. The device of claim 33 wherein the means for sealing the second sleeve comprises a septum.

37. The device of claim 36 wherein the septum is positioned within the vial receiving chamber.

38. The device of claim 37 wherein the septum has a generally disk shaped portion.

39. The device of claim 38 wherein the septum further comprises a sheath extending axially away from the septum and is dimensioned to fit over one of the piercing ends of the piercing member.

40. The device of claim 39 wherein the sheath has an enlarged distal end that is dimensioned to fit over a portion of a hub that mounts the piercing member.

41. A connector device for establishing fluid communication between a liquid container and vial container comprising:

a sleeve defining a central channel therein for enabling fluid flow therethrough, the sleeve having an inner surface, a piercing member having opposed piercing ends, the piercing member being mounted in the central channel;

means for hermetically sealing the piercing ends when the device is connected to the first container and the second container;

a vial receiving chamber on the sleeve and being adapted to connect to the vial and wherein the vial may be selectively attached to the device without piercing the closure of the vial and without breaching the hermetic seal of the piercing ends; and the sleeve being movable from an inactivated position where fluid cannot flow through the device to an activated position where fluid can flow through the device, the device is capable of being moved from the inactivated position to the activated position by applying a force to the device outside of the first container.

42. A connector device for establishing fluid communication between a liquid container and vial container comprising:

a sleeve defining a central channel therein, the sleeve having an inner surface, a piercing member having opposed piercing ends, the piercing member being mounted in the central channel;

a hub connected to the piercing member slidable within the passageway along the inner surface of the sleeve;

means for hermetically sealing the piercing ends when the device is connected to the first container and the second container;

a vial receiving chamber on the sleeve and being adapted to connect to the vial and wherein the vial may be selectively attached to the device without piercing the closure of the vial and without breaching the hermetic seal of the piercing ends; and the sleeve being movable from an inactivated position where fluid cannot flow through the device to an activated position where fluid can flow through the device, the device is capable of being moved from the inactivated position to the activated position by applying a force to the device outside of the first container.

43. A connector device for establishing fluid communication between a liquid container having a port tube and a vial container comprising:

a sleeve defining a central channel therein, the sleeve having an inner surface, a piercing member having opposed piercing ends, the piercing member being mounted in the central channel;

means for hermetically sealing the piercing ends when the device is connected to the first container and the second container;

a port adaptor positioned on one end of the sleeve, the port adaptor adapted to be fixedly attached to the port tube;

a vial receiving chamber on the other end of the sleeve and being adapted to connect to the vial and wherein the vial may be selectively attached to the device without piercing the closure of the vial and without breaching the hermetic seal of the piercing ends; and, the sleeve being movable from an inactivated position where fluid cannot flow through the device to an activated position where fluid can flow through the device.

44. A connector device for establishing fluid communication between a liquid container and vial container comprising:

a sleeve defining a central channel therein, the sleeve having an inner surface, a piercing member being mounted in the central channel, the piercing member having a first end and an opposed second end;

means for hermetically sealing the first end of the piercing member when the device is connected to the first container and a septum positioned within a vial receiving chamber for sealing the second piercing end of the piercing member, the septum having a ridge;

a vial receiving chamber on the sleeve and being adapted to connect to the vial and wherein the vial may be selectively attached to the device without piercing the closure of the vial and without breaching the hermetic seal of the second end; and, the sleeve being movable from an inactivated position where fluid cannot flow through the device to an activated position where fluid can flow through the device.

* * * * *